US00RE48149E

(19) United States
(12) Reissued Patent
Virr et al.

(10) Patent Number: US RE48,149 E
(45) Date of Reissued Patent: *Aug. 11, 2020

(54) HUMIDIFIER WITH STRUCTURE TO PREVENT BACKFLOW OF LIQUID THROUGH THE HUMIDIFIER INLET

(71) Applicant: ResMed Pty Ltd, Bella Vista, New South Wales (AU)

(72) Inventors: Alexander Virr, Gosford (AU); Ian Malcolm Smith, Sydney (AU); Perry David Lithgow, Sydney (AU); Richard Llewelyn Jones, Hornsby Heights (AU); Andrew Cheung, Sydney (AU)

(73) Assignee: ResMed Pty Ltd, Bella Vista (AU)

( * ) Notice: This patent is subject to a terminal disclaimer.

(21) Appl. No.: 15/706,811

(22) Filed: Sep. 18, 2017

Related U.S. Patent Documents

Reissue of:
(64) Patent No.: 7,614,398
Issued: Nov. 10, 2009
Appl. No.: 11/181,807
Filed: Jul. 15, 2005

U.S. Applications:
(63) Continuation of application No. 15/182,919, filed on Jun. 15, 2016, now Pat. No. Re. 46,571, which is a
(Continued)

(30) Foreign Application Priority Data

Feb. 16, 2001 (AU) ..... PR3117
Aug. 27, 2001 (AU) ..... PR7288

(51) Int. Cl.
*F23D 11/00* (2006.01)
*A61M 15/00* (2006.01)
(Continued)

(52) U.S. Cl.
CPC ..... *A61M 16/16* (2013.01); *A61M 16/109* (2014.02); *A61M 16/0066* (2013.01); *A61M 2205/21* (2013.01); *Y10S 261/65* (2013.01)

(58) Field of Classification Search
CPC ..... A61M 16/16; A61M 16/109; A61M 16/0066; A61M 2205/21; Y10S 261/65
See application file for complete search history.

(56) References Cited

U.S. PATENT DOCUMENTS 1,085,833 A 2/1914 Wilson
1,974,843 A * 9/1934 Blashfield ..... 261/123
(Continued)

FOREIGN PATENT DOCUMENTS

AU 200065475 B2 4/2001
DE 275612 1/1913
(Continued)

OTHER PUBLICATIONS

Extended European Search Report dated Apr. 4, 2018 in European Application No. 17164576.5 (8 pages).
(Continued)

*Primary Examiner* — Joseph A Kaufman
(74) *Attorney, Agent, or Firm* — Nixon & Vanderhye P.C.

(57) ABSTRACT

A humidifier includes a base configured to retain a body of liquid therein, a top cover, and a seal disposed between the top cover and the base. At least a portion of the base is constructed of a heat conducting material. The top cover defines both an inlet and an outlet communicated with an interior of the base. The inlet is configured to receive pressurized breathable gas and the outlet is configured to deliver the pressurized breathable gas with added humidity.

43 Claims, 20 Drawing Sheets

Related U.S. Application Data continuation of application No. 13/944,960, filed on Aug. 23, 2013, now Pat. No. Re. 46,079, said application No. 13/944,960 is a continuation of application No. 13/100,783, filed on May 4, 2011, now Pat. No. Re. 44,453, which is an application for the reissue of Pat. No. 7,614,398, said application No. 13/100,783 is a continuation of application No. 10/467,382, filed as application No. PCT/AU02/00155 on Feb. 14, 2002, now Pat. No. 6,935,337.

(51) Int. Cl.

| | |
|---|---|
| ***F23D 14/00*** | (2006.01) |
| ***A61M 16/16*** | (2006.01) |
| ***A61M 16/10*** | (2006.01) |
| *A61M 16/00* | (2006.01) |

(56) References Cited

U.S. PATENT DOCUMENTS

| | | | | |
|---|---|---|---|---|
| RE19,826 | E | | 1/1936 | Aisenstein |
| 2,220,669 | A | | 11/1940 | Allen |
| 2,780,708 | A | | 2/1957 | Glynn et al. |
| 2,945,619 | A | | 7/1960 | Ballard |
| 3,171,353 | A | | 3/1965 | McMahan |
| 3,316,910 | A | | 5/1967 | Davis |
| 3,584,401 | A | | 6/1971 | Cryer et al. |
| 3,612,710 | A | | 10/1971 | Mount |
| 3,620,638 | A | | 11/1971 | Kaye et al. |
| 3,638,926 | A | | 2/1972 | Melville et al. |
| 3,659,604 | A | | 5/1972 | Melville et al. |
| 3,690,317 | A | | 9/1972 | Millman |
| 3,806,102 | A | * | 4/1974 | Valenta et al. ..... 261/142 |
| 3,864,440 | A | * | 2/1975 | Giocoechea ..... 261/122.1 |
| 3,954,920 | A | | 5/1976 | Heath |
| 4,037,994 | A | | 7/1977 | Bird |
| 4,051,205 | A | * | 9/1977 | Grant ..... 261/70 |
| 4,152,379 | A | | 5/1979 | Suhr |
| 4,171,190 | A | | 10/1979 | Hudson |
| 4,222,971 | A | * | 9/1980 | Eilert ..... 261/92 |
| 4,229,142 | A | | 10/1980 | Le Dall et al. |
| 4,237,080 | A | | 12/1980 | Elliott |
| 4,243,396 | A | * | 1/1981 | Cronenberg ..... 96/311 |
| 4,336,798 | A | | 6/1982 | Beran |
| 4,383,800 | A | | 5/1983 | Becker et al. |
| 4,523,896 | A | | 6/1985 | Lhenry et al. |
| 4,532,088 | A | * | 7/1985 | Miller ..... 261/142 |
| 4,576,616 | A | | 3/1986 | Mottram et al. |
| 4,588,425 | A | | 5/1986 | Usry et al. |
| 4,621,632 | A | | 11/1986 | Bartels et al. |
| 4,657,713 | A | | 4/1987 | Miller |
| 4,686,354 | A | | 8/1987 | Makin |
| 4,753,758 | A | | 6/1988 | Miller |
| 4,799,287 | A | | 1/1989 | Belanger |
| 4,802,819 | A | | 2/1989 | Bevington |
| 4,807,616 | A | * | 2/1989 | Adahan ..... 128/204.21 |
| 4,838,258 | A | | 6/1989 | Dryden et al. |
| 4,906,417 | A | | 3/1990 | Gentry |
| 4,913,140 | A | | 4/1990 | Orec et al. |
| 4,921,642 | A | | 5/1990 | Latorraca |
| 4,926,856 | A | | 5/1990 | Cambio et al. |
| 4,941,469 | A | | 7/1990 | Adahan |
| 4,946,348 | A | | 8/1990 | Yapp |
| 4,953,546 | A | * | 9/1990 | Blackmer et al. ..... 128/203.16 |
| 4,973,234 | A | | 11/1990 | Swenson |
| 4,993,411 | A | | 2/1991 | Callaway |
| 5,097,424 | A | | 3/1992 | Ginevri et al. |
| 5,127,800 | A | | 7/1992 | Hyll et al. |
| 5,199,009 | A | | 3/1993 | Svast |
| 5,231,979 | A | * | 8/1993 | Rose et al. ..... 128/204.14 |
| 5,237,987 | A | | 8/1993 | Anderson et al. |
| 5,271,391 | A | | 12/1993 | Graves |
| 5,329,939 | A | | 7/1994 | Howe |
| 5,391,063 | A | | 2/1995 | Hantle et al. |
| 5,443,061 | A | | 8/1995 | Champain et al. |
| 5,445,143 | A | | 8/1995 | Sims |
| 5,474,112 | A | | 12/1995 | Carola |
| 5,482,031 | A | | 1/1996 | Lambert |
| 5,537,997 | A | | 7/1996 | Mechlenburg et al. |
| 5,558,084 | A | * | 9/1996 | Daniell et al. ..... 128/203.17 |
| 5,564,415 | A | | 10/1996 | Dobson et al. |
| 5,577,496 | A | | 11/1996 | Blackwood et al. |
| 5,588,423 | A | | 12/1996 | Smith |
| 5,598,837 | A | | 2/1997 | Sirianne et al. |
| 5,651,775 | A | | 7/1997 | Walker et al. |
| 5,655,522 | A | | 8/1997 | Mechlenburg et al. |
| 5,673,687 | A | | 10/1997 | Dobson et al. |
| 5,794,219 | A | | 8/1998 | Brown |
| 5,822,715 | A | | 10/1998 | Worthington et al. |
| 5,828,943 | A | | 10/1998 | Brown |
| 5,832,448 | A | | 11/1998 | Brown |
| 5,848,592 | A | | 12/1998 | Sibley |
| 5,870,283 | A | | 2/1999 | Maeda et al. |
| 5,879,163 | A | | 3/1999 | Brown et al. |
| 5,887,133 | A | | 3/1999 | Brown et al. |
| 5,888,053 | A | | 3/1999 | Kobayashi et al. |
| 5,897,493 | A | | 4/1999 | Brown |
| 5,899,855 | A | | 5/1999 | Brown |
| 5,913,310 | A | | 6/1999 | Brown |
| 5,916,493 | A | | 6/1999 | Miller et al. |
| 5,918,603 | A | | 7/1999 | Brown |
| 5,933,136 | A | | 8/1999 | Brown |
| 5,940,801 | A | | 8/1999 | Brown |
| 5,943,473 | A | | 8/1999 | Levine |
| 5,951,300 | A | | 9/1999 | Brown |
| 5,956,501 | A | | 9/1999 | Brown |
| 5,960,403 | A | | 9/1999 | Brown |
| 5,985,559 | A | | 11/1999 | Brown |
| 5,997,476 | A | | 12/1999 | Brown |
| D419,658 | S | | 1/2000 | Matchett et al. |
| 6,023,686 | A | | 2/2000 | Brown |
| 6,032,119 | A | | 2/2000 | Brown et al. |
| 6,050,260 | A | | 4/2000 | Daniell et al. |
| 6,101,478 | A | | 8/2000 | Brown |
| 6,109,865 | A | | 8/2000 | Ishikawa |
| 6,129,524 | A | | 10/2000 | Wollenweber et al. |
| 6,131,571 | A | | 10/2000 | Lampotang et al. |
| 6,135,432 | A | | 10/2000 | Hebblewhite et al. |
| 6,144,837 | A | | 11/2000 | Quy |
| 6,152,132 | A | | 11/2000 | Psaros |
| 6,158,978 | A | | 12/2000 | Norbury, Jr. |
| 6,161,095 | A | | 12/2000 | Brown |
| 6,185,095 | B1 | | 2/2001 | Helot et al. |
| 6,189,870 | B1 | | 2/2001 | Withall |
| 6,202,991 | B1 | | 3/2001 | Coniglio et al. |
| 6,210,116 | B1 | | 4/2001 | Kuczaj et al. |
| 6,213,119 | B1 | | 4/2001 | Brydon et al. |
| 6,216,691 | B1 | | 4/2001 | Kenyon et al. |
| 6,257,171 | B1 | | 7/2001 | Rivard |
| 6,279,574 | B1 | | 8/2001 | Richardson et al. |
| 6,308,706 | B1 | | 10/2001 | Lammers et al. |
| 6,332,462 | B1 | | 12/2001 | Krohn |
| 6,338,473 | B1 | | 1/2002 | Hebblewhite et al. |
| 6,340,288 | B1 | | 1/2002 | Hulkkonen et al. |
| 6,349,724 | B1 | | 2/2002 | Burton et al. |
| D454,393 | S | | 3/2002 | Lynch et al. |
| 6,397,841 | B1 | | 6/2002 | Kenyon et al. |
| 6,398,197 | B1 | | 6/2002 | Dickinson |
| 6,435,180 | B1 | * | 8/2002 | Hewson et al. ..... 128/204.18 |
| 6,471,493 | B2 | | 10/2002 | Choi et al. |
| D467,335 | S | | 12/2002 | Lithgow et al. |
| D468,011 | S | | 12/2002 | Lynch et al. |
| D468,017 | S | | 12/2002 | McCombs |
| 6,514,053 | B2 | | 2/2003 | Takura et al. |
| 6,543,449 | B1 | | 4/2003 | Woodring et al. |
| 6,554,260 | B1 | * | 4/2003 | Lipscombe et al. ..... 261/142 |
| 6,591,834 | B1 | | 7/2003 | Colla et al. |
| 6,604,390 | B1 | | 8/2003 | Nooner |
| 6,615,444 | B2 | | 9/2003 | McGilll et al. |
| 6,622,724 | B1 | | 9/2003 | Truitt et al. |
| 6,672,300 | B1 | | 1/2004 | Grant |
| D487,311 | S | | 3/2004 | Lithgow et al. |
| 6,718,974 | B1 | * | 4/2004 | Moberg ..... 128/204.14 |

(56) References Cited

U.S. PATENT DOCUMENTS

| | | | | |
|---|---|---|---|---|
| D493,520 | S | 7/2004 | Bertinetti et al. | |
| D493,884 | S | 8/2004 | Virr et al. | |
| 6,772,999 | B2 | 8/2004 | Lipscombe et al. | |
| 6,775,882 | B2 | 8/2004 | Murphy et al. | |
| D498,527 | S | 11/2004 | Virr et al. | |
| 6,827,340 | B2 | 12/2004 | Austin et al. | |
| 6,837,260 | B1 | 1/2005 | Kuehn | |
| 6,874,771 | B2 | 4/2005 | Birdsell et al. | |
| 6,896,478 | B2 | 5/2005 | Botros et al. | |
| 6,910,483 | B2 | 6/2005 | Daly et al. | |
| 6,918,389 | B2 | 7/2005 | Seakins et al. | |
| 6,935,337 | B2 * | 8/2005 | Virr et al. | 128/203.16 |
| 7,096,864 | B1 | 8/2006 | Mayer et al. | |
| 7,111,624 | B2 | 9/2006 | Thudor et al. | |
| 7,137,388 | B2 * | 11/2006 | Virr et al. | 128/203.17 |
| 7,225,809 | B1 | 6/2007 | Bowen et al. | |
| 7,413,173 | B2 | 8/2008 | DiMatteo et al. | |
| 7,614,398 | B2 | 11/2009 | Virr et al. | |
| 7,616,871 | B2 | 11/2009 | Kramer | |
| 7,677,246 | B2 | 3/2010 | Kepler et al. | |
| 8,091,547 | B2 | 1/2012 | Thudor et al. | |
| RE44,453 | E | 8/2013 | Virr et al. | |
| 8,550,072 | B2 | 10/2013 | Thudor et al. | |
| RE46,079 | E | 7/2016 | Virr et al. | |
| 2001/0017134 | A1 | 8/2001 | Bahr | |
| 2002/0020930 | A1 | 2/2002 | Austin et al. | |
| 2002/0022973 | A1 | 2/2002 | Sun et al. | |
| 2002/0056453 | A1 | 5/2002 | Klopp et al. | |
| 2002/0159897 | A1 | 10/2002 | Kegg et al. | |
| 2003/0062045 | A1 | 4/2003 | Woodring et al. | |
| 2003/0084900 | A1 | 5/2003 | LeClerc et al. | |
| 2003/0115085 | A1 | 6/2003 | Satoh | |
| 2003/0208465 | A1 | 11/2003 | Yurko et al. | |
| 2003/0230308 | A1 | 12/2003 | Linden | |
| 2004/0035422 | A1 | 2/2004 | Truitt et al. | |
| 2004/0055597 | A1 | 3/2004 | Virr et al. | |
| 2004/0060559 | A1 | 4/2004 | Virr et al. | |
| 2005/0005937 | A1 | 1/2005 | Farrugia et al. | |
| 2005/0103339 | A1 | 5/2005 | Daly et al. | |
| 2005/0217673 | A1 | 10/2005 | Daly et al. | |
| 2006/0191531 | A1 | 8/2006 | Mayer | |
| 2006/0237005 | A1 | 10/2006 | Virr et al. | |
| 2007/0036662 | A1 | 2/2007 | Pensola et al. | |
| 2007/0134085 | A1 | 6/2007 | Daly et al. | |
| 2009/0229606 | A1 | 9/2009 | Tang et al. | |
| 2010/0229867 | A1 | 9/2010 | Bertinetti et al. | |

FOREIGN PATENT DOCUMENTS

| | | | |
|---|---|---|---|
| DE | 30 05 094 | A1 | 8/1981 |
| DE | 3623162 | A1 | 7/1986 |
| DE | 9014848 | | 3/1991 |
| DE | 4138098 | C2 | 11/1991 |
| DE | 4244493 | A1 | 7/1993 |
| DE | 93 17 450 | | 6/1994 |
| DE | 3789221 | T2 | 8/1994 |
| DE | 9409231.1 | U1 | 12/1994 |
| DE | 195 15 739 | A1 | 11/1996 |
| DE | 19630466 | | 2/1998 |
| DE | 694 09 024 | T2 | 10/1998 |
| DE | 29817685 | U1 | 10/1998 |
| DE | 29909611 | U1 | 10/1999 |
| DE | 199 36 499 | A1 | 2/2001 |
| DE | 10016005 | A1 | 12/2001 |
| DE | 102005007773 | A1 | 9/2005 |
| EP | 0 201 985 | A1 | 11/1986 |
| EP | 0 274 996 | A2 | 7/1988 |
| EP | 3823242 | A1 | 2/1990 |
| EP | 0 376 584 | A2 | 7/1990 |
| EP | 0 589 429 | A1 | 3/1994 |
| EP | 0 589 429 | B1 | 3/1994 |
| EP | 0 845 277 | A2 | 6/1998 |
| EP | 0 893 750 | | 1/1999 |
| EP | 0 903 160 | A1 | 3/1999 |
| EP | 1023912 | A2 | 8/2000 |
| EP | 1 055 431 | A2 | 11/2000 |
| EP | 1 087 322 | A2 | 3/2001 |
| EP | 1318307 | | 6/2003 |
| EP | 1 374 938 | A1 | 1/2004 |
| FR | 2 323 436 | | 4/1977 |
| FR | 2 714 985 | | 7/1995 |
| GB | 1556492 | A | 11/1979 |
| GB | 2177006 | A | 1/1987 |
| JP | 7-145795 | A | 6/1995 |
| JP | 11-398 | A | 1/1999 |
| JP | 2000-337670 | A | 12/2000 |
| JP | 2001-160102 | A | 6/2001 |
| JP | 2002-206498 | A | 7/2002 |
| JP | 2002-253672 | | 9/2002 |
| JP | 2002-306601 | | 10/2002 |
| WO | WO 93/05451 | A1 | 3/1993 |
| WO | WO 95/15778 | A1 | 6/1995 |
| WO | WO 97/32619 | A1 | 9/1997 |
| WO | WO 98/04311 | A1 | 2/1998 |
| WO | WO 98/31937 | A1 | 7/1998 |
| WO | WO 98/33433 | | 8/1998 |
| WO | WO 98/57691 | A1 | 12/1998 |
| WO | WO 99/13932 | | 3/1999 |
| WO | WO 99/22794 | A1 | 5/1999 |
| WO | WO 99/64747 | | 12/1999 |
| WO | WO 00/21602 | A1 | 4/2000 |
| WO | WO 00/27457 | A1 | 5/2000 |
| WO | WO 00/32261 | A1 | 6/2000 |
| WO | WO 01/10489 | A2 | 2/2001 |
| WO | WO 01/32069 | A2 | 5/2001 |
| WO | WO 01/73653 | A1 | 10/2001 |
| WO | WO 02/02169 | A1 | 1/2002 |
| WO | WO 02/066106 | A1 | 8/2002 |
| WO | WO 02/066107 | A1 | 8/2002 |
| WO | WO 2007/019628 | A1 | 2/2007 |
| WO | WO 2009/059359 | A1 | 5/2009 |
| WO | WO 2009/156921 | A1 | 12/2009 |
| WO | WO 2010/092496 | | 8/2010 |

OTHER PUBLICATIONS

J. H. Emerson Co., Cough Assist, "Non-Invasive Removal of Bronchial Secretions," 2 pages.

Madaus Schwarzer Medizintechnik, "New Approaches in Diagnosis and Therapy—Moritz biLevel User Manual", May 1994, 38 pages.

German Patient Manual for Hoffrichter/Sandmann CPAP Respirator—Perfect CPAP Therapy, 30 pages plus Translation Verification Certificate, Mar. 1998.

Breas Medical AB "iSleep® 20" Brochure, Dec. 2007, 2 pages.

Fisher & Paykel Healthcare "SleepStyle™ 600 CPAP Series" Specification Sheet, 2005, 4 pages.

Fisher & Paykel Healthcare Two Easy Steps to Comfort, Humidification and Nasal CPAP Therapy, Aug. 1995, 4 pages.

Hoffrichter GmbH "Vector therapy in perfection" Brochure, 2002, 2 pages.

MAP Medizin-Technologie GmbH "minni II Max nCPAP®, The respiratory therapy device with out an integrated humidifier", Dec. 2003, 17 pages.

MAP Medizintechnik fuer Arzt and Patient "max II nCPAP moritz II biLevel—The gentle therapy for sleep-related breathing disorders" Brochure, 2000, 4 pages.

Respironics "System One Heated Humidifier User Manual", May 2009, 20 pages.

ResMed, "The Sullivan® HumidAire™", 1997, 1 page.

De Vilbiss® Healthcare, "DeVilbiss IntelliPAP® Standard CPAP System," Nov. 2007, 2 pages.

Photos of HumidAire™, 11 pages.

Photos of tray system available before the critical date, with sample flow generator and humidifier, 5 pages.

Microfilm of Japanese Utility-Model Application No. S54-003858 (Japanese Utility-Model Application Publication No. S55-104925).

MAP Medizintechnik, "minni Max nCPAP®" brochure, 12 pages, Mar. 2005.

MAP Medizintechnik, "Moritz II biLEVEL®—The gentle therapy for sleep-related breathing disorders" brochure, 6 pages, Jan. 2001.

(56) References Cited

OTHER PUBLICATIONS

Photos of MAP Humidifier and Tub, 2 pages and cover sheet, undated.
Madaus Schwarzer Medizintechnik, "New Approaches in Diagnosis and Therapy—Max nCPAP User Manual", Mar. 1994, 38 pages.
ResMed "Sullivan® HumidAire® User's Instructions", 8 pages, 1998.
MAP Medizin-Technologie GmbH, Moritz® S/Moritz® ST—Sailing toward therapeutic success . . . , Jul. 2004, 4 pages.
Hoffrichter "Vector CPAP—Therapy With Technical Mastery", 4 pages, Oct. 1998.
Fischer & Paykel, "Two Easy Steps to Comfort", 4 pages, Aug. 1995.
Notification of Second Office Action dated Jan. 27, 2006 in Chinese Appln. No. 02804936.5, with English Translation (6 pages).
Notification of Reasons for Rejection dated Feb. 19, 2008 in Japanese Appln. No. 2002-565664, with English translation (5 pages).
Final Notice of Reasons for Rejection delivered Sep. 24, 2008 in Japanese Appln. No. 2002-565664, with English translation (6 pages).
Notification of the First Office Action dated Jul. 22, 2005 in Chinese Appln. No. 02804936.5, with English translation (8 pages).
Extended European Search Report dated Apr. 28, 2011 in European Appln. No. 10189422.8 (5 pages).
International Search Report dated Mar. 21, 2002 in International Appln. No. PCT/AU02/00155 (2 pages).
International Preliminary Examination Report completed Oct. 4, 2002 in International Appln. No. PCT/AU02/00155 (3 pages).
Office Action dated Jan. 22, 2008 in Japanese Patent Appln. No. 2002-565665 (w/English translation) (12 pages).
Examination Report dated Oct. 10, 2003 in New Zealand Appln. No. 527088 (2 pages).
Supplementary European Search Report dated Sep. 15, 2009 in European Appln. No. 02700014.0, (3 pages).
Communication dated Jul. 1, 2010 in European Appln. No. 02 700 014.0 (5 pages).
Extended European Search Report dated May 4, 2012 in European Appln. No. 12159042.6 (5 pages).
ITC Action related to Certain Sleep-Disordered Breathing Treatment Systems and Components Thereof, Inv. No. 337-TA-_, CBI 13-185, filed on Mar. 28, 2013, 57 pages.
ResMed's First Amended Complaint for Patent Infringement, filed in the United States District Court Central District of California Southern Division, filed on Apr. 8, 2013, 342 pages.
"Complaint for Patent Infringement—Jury Trial Demanded" as filed in the United States District Court, Southern District of California, Case No. '13CV1246 MMAWMC, dated May 31, 2013, 18 pages.
"Motion to Amend the Complaint and Notice of Investigation" as filed in the United States International Trade Commission, Investigation No. 337-TA-879, dated May 31, 2013, 18 pages.
Petition for *Inter Partes* Review of U.S. Pat. No. 7,614,398, dated Aug. 16, 2013.
Declaration of Joseph Dyro, Petition Exhibit 1007.
Notification of Acceptance of Request for Invalidation and English Translation for corresponding Chinese Pat. No. 02804936.5, dated Mar. 20, 2014, 188 pages.
Petition for *Inter Parties* Review of U.S. Pat. No. Re. 44,453 Under to 35 U.S.C. §§ 311 ET SEQ. and 37 C.F.R. §42.100 ET SEQ., *Apex Medical Corp.*, Petitioner v. *ResMed Limited*, Patent Owner, Case No. IPR2014-00551, Mar. 27, 2014, 38 pages.
Apex Medical Corporation, Petition Exhibit 1002 in IPR2014-00551, "ResMed's First Amended Complaint for Patent Infringement—Jury Trial Demanded", Case No. SACV-13-00498 CJC (RNBx), USDC, Central District of California, Southern Division, 18 pages.
Petition Exhibit 1006 in IPR2014-00551, Patent Owner Amendment dated Mar. 27, 2009, in U.S. Appl. No. 11/181,807, 10 pages.
Petition Exhibit 1007 in IPR2014-00551, Declaration of Joseph Dyro in Support of *Inter Partes* Review of U.S. Pat. Re. 44,453, executed Mar. 26, 2014, 15 pages.
Petition for *Inter Parties* Review of U.S. Pat. No. Re. 44,453 Under to 35 U.S.C. §§311-319 and 37 C.F.R. §42.100 et seq., *BMC Medical Co. Ltd.*, Petitioner v, *ResMed Limited*, Patent Owner, Case No. IPR2014-01196, Jul. 23, 2014, 62 pages.
Petition Exhibit 1003 in IPR2014-01196, REMStar® Heated Humidifier Manual, Mar. 15, 2001, 8 pages.
Petition Exhibit 1004 in IPR2014-01196, Declaration of Steve Bordewick, Jul. 22, 2014, 59 pages.
Petition Exhibit 1006 in IPR2014-01196, Patent Owner ResMed Limited's Preliminary Response filed Jul. 10, 2014, in IPR2014-00551, 41 pages.
Petition Exhibit 1007 in IPR2014-01196, ITC Investigation No. 337-TA-890,: Order No. 7: Initial Determination Granting Complainants' Motion to Amend Complaint and Notice of Investigation and Granting Respondents' Motion to Terminate the Investigation with Respect to U.S. Pat. No. 7,614,398, served Feb. 4, 2014, 8 pages.
Petition Exhibit 1008 in IPR2014-01196, Case No. 13-cv-1246-CAB (WMc), Order on Motion to Stay, Motion to Dismiss, and Related Discovery Request, Oct. 15, 2013, 3 pages.
Petition Exhibit 1009 in IPR2014-01196, Case No. SACV 13-00498: Order Granting Defendants' Motion to Stay Litigation Pending *Inter Partes* Review, Oct. 4, 2013, 3 pages.
Petition Exhibit 1010 in IPR2014-01196: Patent Prosecution History of Reissue U.S. Appl. No. 13/944,960, filed Jul. 18, 2013, 228 pages.
Petition Exhibit 1011 in IPR2014-01196: Patent Prosecution History of U.S. Pat. No. 7,614,398, 174 pages.
Petition Exhibit No. 1012 in IPR2014-01196: Patent Prosecution History of U.S. Pat. No. Re. 44,453, 2157 pages.
Petition Exhibit No. 1013 in IPR2014-01196: Proof of Service of 3B Medical, Inc. In Civil Action No. 13-cv-1246-MMA-WMC, 5 pages.
Petition Exhibit No. 1014 in IPR2014-01196: Australian Application No. PR 3117, filed Feb. 16, 2001, 17 pages.
Petition Exhibit No. 1015 in IPR2014-01196: ITC Investigation No. 337-TA-890: Order No. 8: Construing Terms of the Asserted Patents, served Jan. 17, 2014, 51 pages.
Petition Exhibit No. 1016 in IPR2014-01196: ITC Investigation No. 337-TA-890: Order No. 14: Denying Respondents' Motion for Summary Determination of Invalidity of U.S. Pat. No. Re. 44,453, served Mar. 26, 2014, 19 pages.
Petition Exhibit No. 1020 in IPR2014-01196: Australian Application No. PR 7288, filed Aug. 27, 2001, 23 pages.
Petition Exhibit No. 1022 in IPR2014-01196: ITC Investigation No. 337-TA-890: Notice of Commission Determination Not to Review an Initial Determination Granting the Complainants' Motion to Amend the Complaint and Notice of Investigation to Substitute U.S. Pat. No. Re. 44,453 for U.S. Pat. No. 7,614,398 and Granting Respondents'Motion to Terminate the Investigation with Respect to U.S. Pat. No. 7,614,398, Issued: Feb. 10, 2014, 3 pages.
Patent Owner Exhibit No. 2001 in IPR2014-00551, Applicant Transmittal to USPTO re Completion of National Phase Filing of the PCT Application for the Mayer Reference, Aug. 6, 2002, 4 pages.
Patent Owner Exhibit No. 2002 in IPR2014-00551, Re. 44,453 Patent Application Data Sheet, Initial May 4, 2011, 5 pages.
Patent Owner Exhibit No. 2003 in IPR2014-00551, Decision of the Patent Trial and Appeal Board Denying Institution of *Inter Partes* Review of U.S. Pat. No. 7,614,398, entered Feb. 20, 2014, 5 pages.
Patent Owner Exhibit No. 2005 in IPR2014-00551, U.S. National Stage Worksheet of USPTO re National Phase Requirements Completion for the Mayer Reference, 1 page.
Patent Owner Exhibit No. 2010 in IPR2014-00551, Deposition Transcript of Dr. Joseph F. Dyro in Connection with *Inter Partes* Review Proceedings IPR2013-00511, IPR2013-00512, IPR2013-00514, IPR2013-00515, and IPR2013-00516, Apr. 21, 2014, 46 pages.
Patent Owner Exhibit No. 2011 in IPR2014-00551, Patent Owner ResMed Limited's Preliminary Response to Apex Medical Corp.'s Petition for *Inter Partes* Review of U.S. Pat. No. 7,614,398, Case No. IPR2013-00513, Nov. 22, 2013, 15 pages.

(56) References Cited

OTHER PUBLICATIONS

Petition for *Inter Parties* Review of U.S. Pat. No. Re. 44,453, *BMC Medical Co. Ltd.*, Petitioner v. *ResMed Limited*, Patent Owner, Case No. IPR2014-01363, Aug. 22, 2014, 66 pages.
Petition Exhibit 1004 in IPR2014-01363, Declaration of Steve Bordewick, Aug. 22, 2014, 90 pages.
Notification of Acceptance of Request for Invalidation, Issued: Dec. 24, 2014, in Chinese Pat. No. 02804936.5, with English translation, 62 pages.
U.S. International Trade Commission, Inv. No. 337-TA-890, "Office of Unfair Import Investigations' Petition for Review of the Initial Determination," dated Sep. 3, 2014 (Public Version Filed: Oct. 8, 2014), 34 pages.
U.S. International Trade Commission, Inv. No. 337-TA-890, "Office of Unfair Import Investigations' Response to the Petitions for Review of the Initial Determination," dated Sep. 11, 2014 (Public Version Filed: Oct. 8, 2014), 37 pages.
U.S. International Trade Commission, Inv. No. 337-TA-890, "Office of Unfair Import Investigations' Reply to the Private Parties' Responses to the Commission Question," dated Nov. 7, 2014 (Public Version Filed: Dec. 3, 2014), 19 pages.
U.S. International Trade Commission, Inv. No. 337-TA-890, "Office of Unfair Import Investigations' Response to ResMed's Motion to Withdraw the '487 Patent or Alternatively Find No Violation Based on Technical Prong," dated Nov. 19, 2014 (Public Version Filed: Dec. 3, 2014), 5 pages.
U.S. International Trade Commission, Inv. No. 337-TA-890, "Notice of the Commission's Final Determination; Issuance of a Limited Exclusion Order and Cease and Desist Orders; Termination of the Investigation," Issued: Dec. 23, 2014, 25 pages.
U.S. Patent and Trademark Office, Case IPR2014-01196, U.S. Pat. No. Re. 44,453 E, "Decision Institution of *Inter Partes* Review 37 C.F.R. §42.108," Paper No. 7, Entered: Dec. 21, 2014, 11 pages.
U.S. Patent and Trademark Office, Case IPR2014-01196 and IPR2014-01363, U.S. Pat. No. Re. 44,453 E, "Scheduling Order," Entered: Jan. 21, 2015, 9 pages.
U.S. Patent and Trademark Office, Case IPR2014-01363, U.S. Pat. No. Re. 44,453 E, Decision Institution of *Inter Partes* Review 37 C.F.R. §42.108, Paper No. 7, Entered: Jan. 21, 2015, 21 pages.
Communication Pursuant to Article 94(3) EPC dated Feb. 4, 2015 in European Application No. 12 159 042.6 (4 pages).
Fisher & Paykel Limited, New Zealand Application No. 503495, filed Mar. 21, 2000, 29 pages.
Communication pursuant to Article 94(3) EPC (examination report) dated Jun. 5, 2015 in European Application No. 10 189 422.8 (4 pages).
Communication pursuant to Article 94(3) EPC (examination report) dated Jun. 12, 2015 in European Application No. 02 700 014.0 (3 pages).
Communication Pursuant to Article 94(3) EPC (European Examination Report) dated Oct. 7, 2015 in EP Application No. 12 159 042.6 (4 pages).
Fisher & Paykel Healthcare, "HC200 Series Nasal CPAP Blower & Heated Humidifier User's Manual", 1998, 17 pages.
Fisher & Paykel Healthcare "SleepStyle™ 200 CPAP Series" Specification Sheet, 2005, 4 pages.
United States Patent and Trademark Office, Before the Patent Trial and Appeal Board, *BMC Medical Co., Ltd., 3B Products, L.L.C. and 3B Medical Inc.* (Petitioner) v. *ResMed Limited* (Patent Owner), Final Written Decision, Paper 25, Entered Jan. 20, 2016 in IPR2014-01363 (39 pages).
United States Patent and Trademark Office, Before the Patent Trial and Appeal Board, *BMC Medical Co., Ltd., 3B Products, L.L.C. and 3B Medical Inc.* (Petitioner) v. *ResMed Limited* (Patent Owner), Final Written Decision, Paper 25, Entered Jan. 19, 2016 in IPR2014-01196 (14 pages).
Virr et al., U.S. Appl. No. 15/182,919, filed Jun. 15, 2016, entitled Humidifier with Structure to Prevent Backflow of Liquid Through the Humidifier Outlet.

* cited by examiner

HUMIDIFIER WITH STRUCTURE TO PREVENT BACKFLOW OF LIQUID THROUGH THE HUMIDIFIER INLET

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*Notice: More than one reissue application has been filed for the reissue of U.S. Pat. No. 7,614,398. The reissue applications are (i) U.S. application Ser. No. 13/100,783, filed on May 4, 2011, (ii) U.S. application Ser. No. 13/944,960, filed on Aug. 23, 2013, (iii) application Ser. No. 15/182,919, filed Jun. 15, 2016, (iv) application Ser. No. 15/706,811 (the instant application), filed Sep. 18, 2017, (v) application Ser. No. 16/231,286, filed Dec. 21, 2018, and (vi) application Ser. No. 16/232,883, filed Dec. 26, 2018.*

CROSS REFERENCE TO RELATED APPLICATIONS

This application is a continuation *reissue of Ser. No. 15/182,919, filed Jun. 15, 2016, which is a continuation reissue of Ser. No. 13/944,960, filed Aug. 23, 2013, now RE 46,079, which is a continuation reissue of Ser. No. 13/100, 783, now RE 44,453, which is an application for reissue of U.S. Pat. No. 7,614,398, filed as Ser. No. 11/181,807 filed Jul. 15, 2005, which is a continuation* of Ser. No. 10/467, 382, filed 7 Aug. 2003, now U.S. Pat. No. 6,935,337, which is the US national phase of international application PCT/AU02/00155 filed 14 Feb. 2002, which designated the United States, and claims the benefit of Australia Application Nos. PR3117, filed Feb. 16, 2001, and PR 7288, filed Aug. 27, 2001, each of which is incorporated herein by reference in its entirety.

The present application claims priority to Australian Provisional Applications PR3117, filed on Feb. 16, 2001 and PR7288, filed on Aug. 27, 2001, the specifications and drawings of which are incorporated by reference in their entireties.

The present invention relates to a humidifier for use with an apparatus for supplying breathable gas such as those used for Non-invasive Positive Pressure Ventilation (NIPPV) or Continuous Positive Airway Pressure (CPAP).

An apparatus for NIPPV or CPAP typically comprises a blower whose output is connected to a patient interface, such as a mask, via an air delivery conduit. Some patients find NIPPV or CPAP more comfortable when provided with humidified air. To this end, manufacturers often supply humidifiers which may be attached in the air circuit between the blower outlet and the patient interface. Humidifiers typically include a water reservoir and are configured such that ambient air from the blower entering the humidifier collects moisture through contact with the water, before continuing on to the patient interface.

Typically, the blower and humidifier are separate components connected via a flexible conduit. An air delivery conduit connects the humidifier outlet to a patient interface mask. Alternatively, the blower and humidifier may be rigidly-connected together. Air from the blower outlet passes into the humidifier inlet where it is humidified and then passes to the air delivery conduit. A potential problem with either arrangement is that if the humidifier is tilted relative to its normal orientation, water may run or spill from the humidifier into the blower outlet which may damage the electrical circuits of the blower and potentially cause infection control problems.

It is one aspect of the present invention to substantially overcome or at least ameliorate the prior art disadvantages.

It is another aspect to provide a humidifier for a CPAP apparatus that is adapted to substantially prevent liquid contained thereto from undesirably exiting an inlet of the humidifier.

It is another aspect to provide a humidifier that is capable of directly connecting to a CPAP apparatus.

It is another aspect to provide a humidifier that has an inlet that is directly connectable with a CPAP apparatus to effectively eliminate a supply tube.

It is another aspect to provide a humidifier that is capable of heating the liquid contained therein.

One embodiment of the present invention includes an apparatus for humidifying breathable gas including a humidifier body configured to retain a body of liquid therein, an inlet communicated with an interior of the humidifier body and connectable to a blower outlet, and an outlet communicated with the interior of the humidifier body and connectable to a patient supply conduit. The interior of the humidifier is arranged such that liquid from the body of liquid is prevented from exiting the humidifier body through the inlet thereof when the humidifier body is rotated from a working, upright orientation.

In this manner, the liquid is substantially prevented from entering the blower outlet and possibly damaging the blower.

It is contemplated that the apparatus may also include a first chamber having an inlet and an outlet, the first chamber inlet preferably being connectable to a blower outlet, a second chamber having an inlet preferably connected to the first chamber outlet, and an outlet preferably connectable to the patient supply conduit, the second chamber preferably having the carrying capacity for the body of liquid. The first chamber inlet and outlet and volumes of the first and second chambers may be adapted such that, when the humidifier is disposed in the working upright orientation, the body of liquid is contained in the second chamber and, in other relative positions of the humidifier, the body of liquid is retained in at least one of the second chamber and the first and second chambers at a level therewithin below a level of the first chamber inlet.

A volume of the second chamber may be larger than a volume of the first chamber.

The first chamber may be located substantially above the second chamber in the working upright orientation of the apparatus.

The first chamber inlet and outlet may be located adjacent opposing sections of the first chamber.

The second chamber outlet may be located closer to the first chamber outlet than the first chamber inlet.

At least a portion of a base of the second chamber may be made of a heat conducting material.

The heat conductive portion may be in the form of a metallic cap which covers an opening of the base.

The apparatus may also include a top cover, a base, and a divider disposed between the top cover and base, wherein the base defines a receptacle formed therewithin, which preferably retains the body of liquid in the working orientation of the apparatus.

The top cover and the divider together may define the first chamber and the receptacle and the divider together form the second chamber.

The first chamber inlet and the second chamber outlet may be formed in the top cover and is the first chamber outlet and the second chamber inlet may be formed in the divider, the first chamber outlet and the second chamber inlet may be defined by a single aperture in the divider which communicates the first and second chambers.

The divider may define first and second sections, the first section together with the top cover preferably defining the first chamber.

The divider may include a plurality of apertures, separated by ribs, which may provide fluid communication from the second chamber to the second chamber outlet formed in the top cover.

The top cover and the base may be formed from a relatively rigid polymer material and the divider may be formed from a relatively resilient material.

The first chamber inlet may be connected to a blower outlet, the first chamber outlet may be connected to the second chamber inlet, the second chamber outlet may be connected to the patient supply conduit, and a portion of the second chamber below and behind the second chamber inlet may define a volume thereof greater than a volume of the body of liquid.

A portion of the second chamber between the first chamber inlet and the second chamber inlet and below the second chamber inlet may define a volume thereof greater than the volume of the body of liquid.

Portions of the first chamber and second chamber between the first chamber inlet and the second chamber outlet may define a volume thereof greater than the volume of the body of liquid.

Another embodiment of the present invention includes a CPAP apparatus including an apparatus for humidifying breathable gas as described above.

Another embodiment of the present invention includes a humidifier for a CPAP apparatus having a humidifier body defining a fluid reservoir and a fluid passage therein. The humidifier body has first and second chambers with a dividing member therebetween. The dividing member includes an orifice therethrough to communicate the first and second chambers with one another. Air from a blower (not shown) arrives in the first chamber via a first chamber inlet and departs from the second chamber via a second chamber outlet. The fluid passage includes the inlet, outlet, the orifice, and, at least, portions of the first and second chambers. The humidifier is designed to carry a body of liquid having a maximum volume, $V_{max}$. In a working orientation of the humidifier, the liquid body lies in a bottom portion of the second chamber. With respect to the working orientation of the humidifier the orifice lies forward of and to the side of the inlet. The first and second chambers are configured such that a volume of a first portion of the second chamber, which lies directly beneath the fist chamber, is greater than $V_{max}$. Additionally, the volume of a second portion of the second chamber, which is disposed to the side of the first chamber, is greater than $V_{max}$. Furthermore, the volume of a portion of the second chamber forward of the inlet plus a portion of the first chamber forward of the inlet is greater than $V_{max}$. Additionally, the volume of a portion of the second chamber to the side of the inlet plus a portion of the first chamber to the side of the inlet is greater than $V_{max}$.

Yet another embodiment of the present invention includes a humidifier for a CPAP apparatus having first and second chambers, wherein an inlet to the humidifier is communicated with the first chamber, an outlet from the humidifier is communicated with the second chamber, and the first and second chambers are intercommunicated via an orifice extending therebetween. The inlet and orifice are arranged relative to one another such that a level of a volume of liquid present within the humidifier is below at least one of the inlet and orifice for any orientation of the humidifier.

Although certain embodiments of the invention are illustrated and described herein as having certain features, one skilled in the art would recognize that alternative embodiments of the invention could be provided based on at least one or more features, either individually or in combination, of the illustrated and described embodiments.

The benefits of the present invention will be readily appreciated and understood from consideration of the following detailed description of embodiments of this invention, when taken with the accompanying drawings, wherein.

Figure 6:
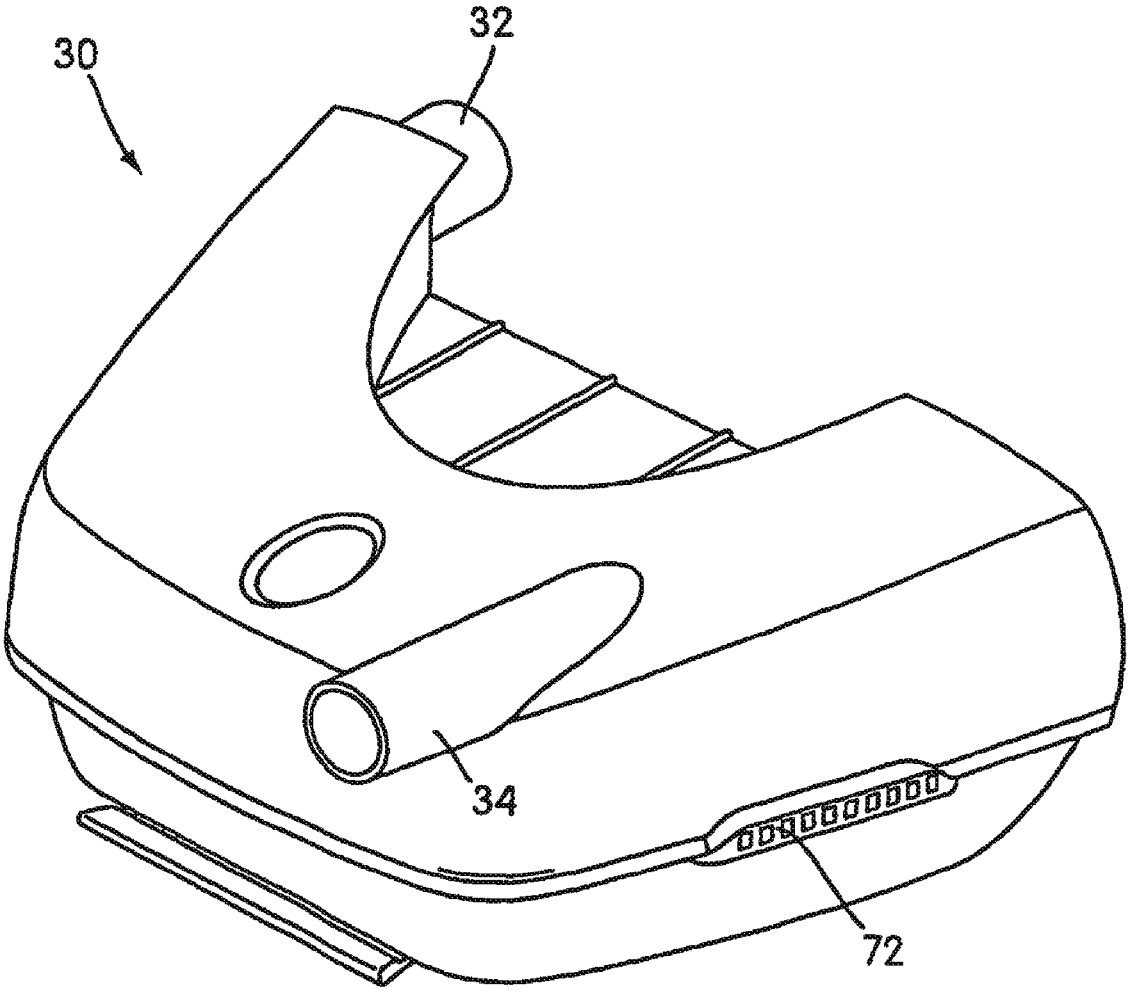
FIG. 6 is a perspective view of a humidifier according to another embodiment of the present invention in a working, upright orientation.
Figure 7:
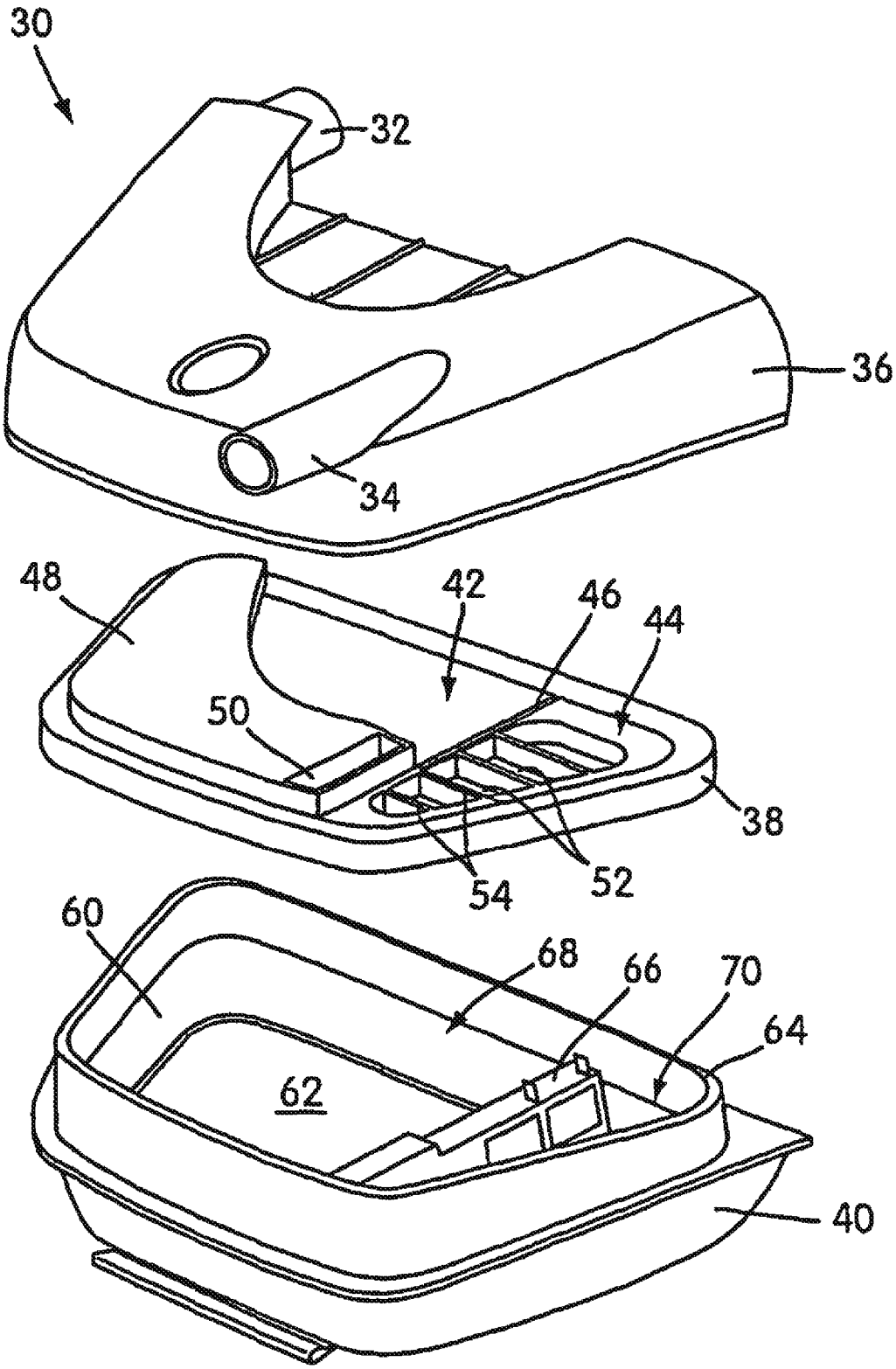
Figure 8:
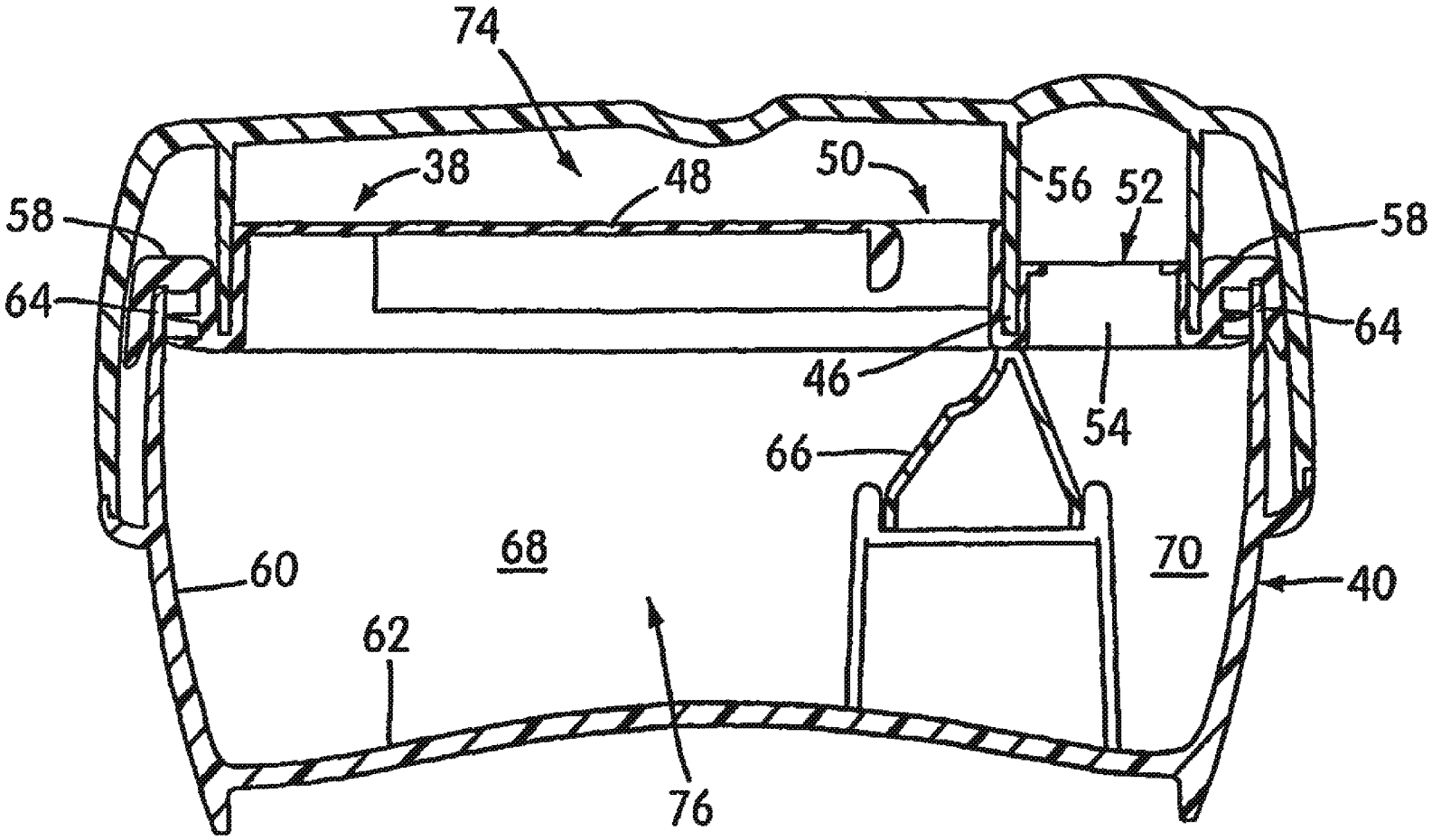
Figure 9:
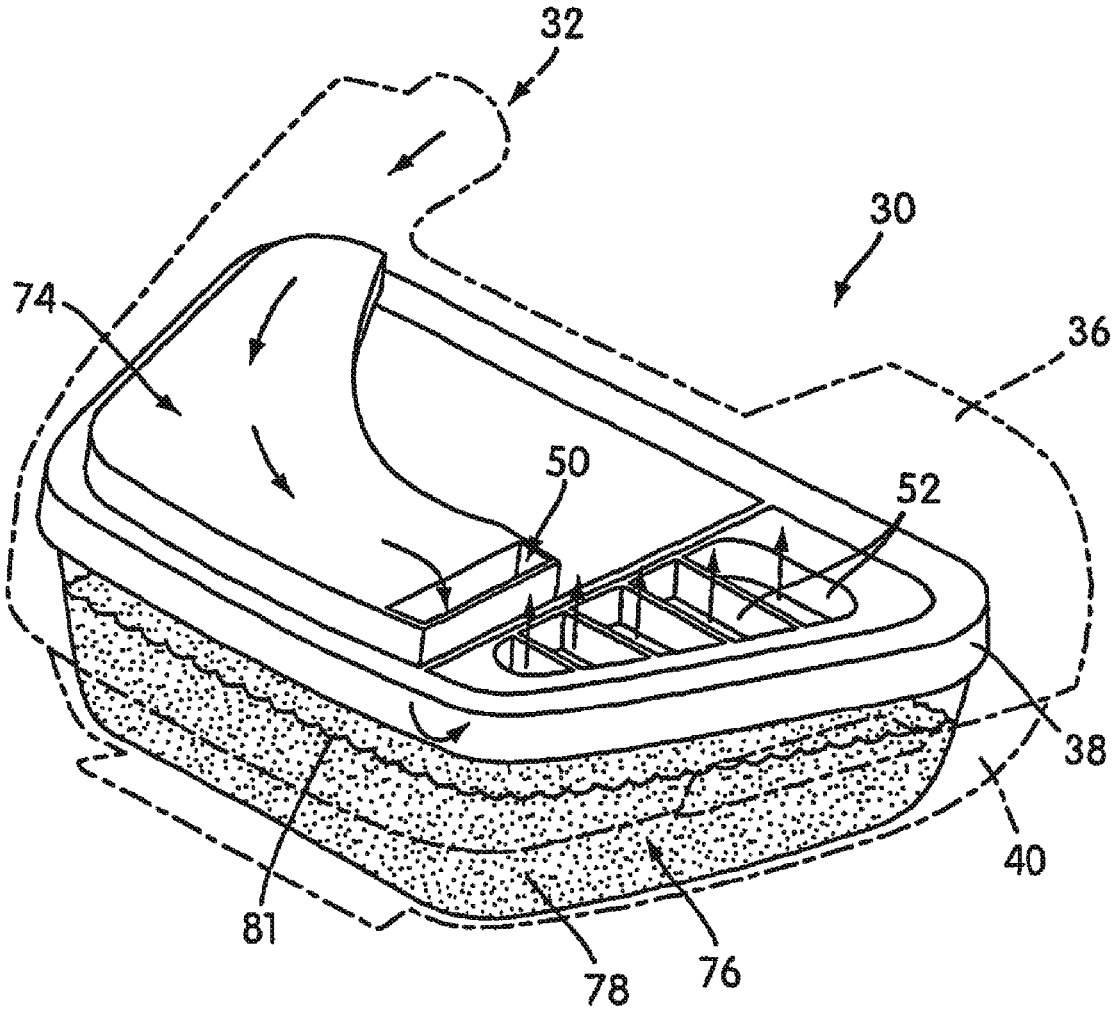
Figure 14:
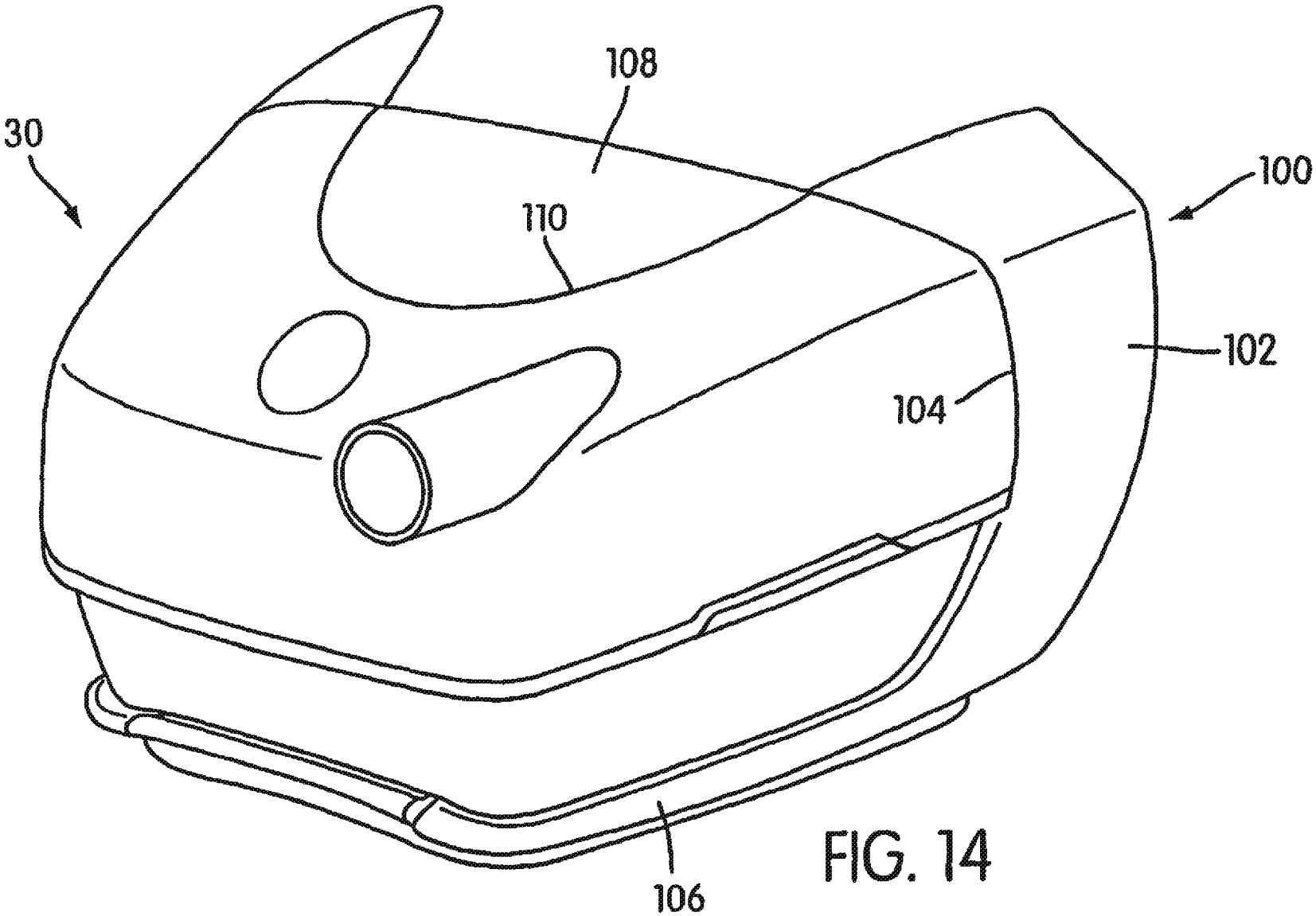
Figure 15:
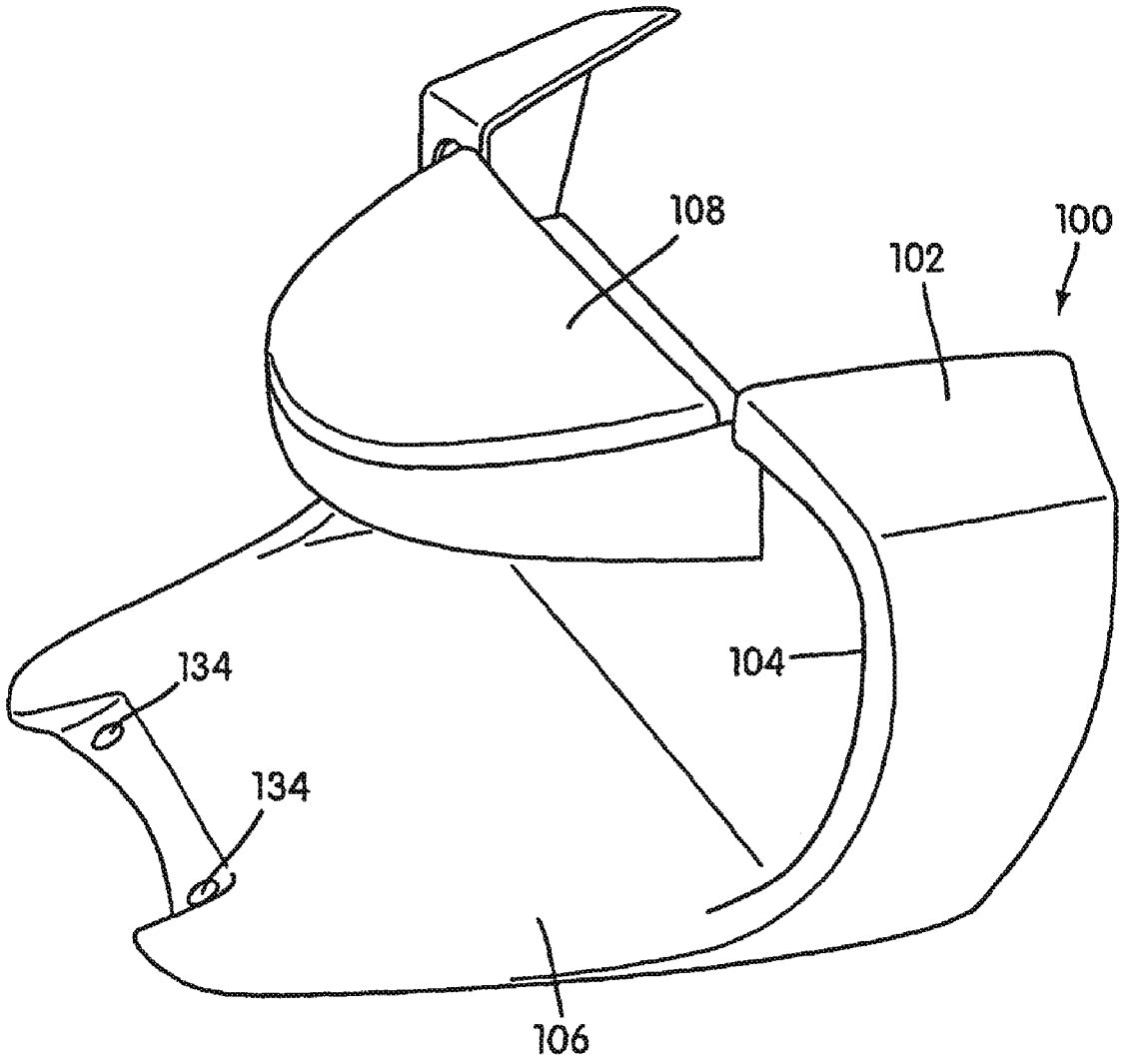
Figure 16:
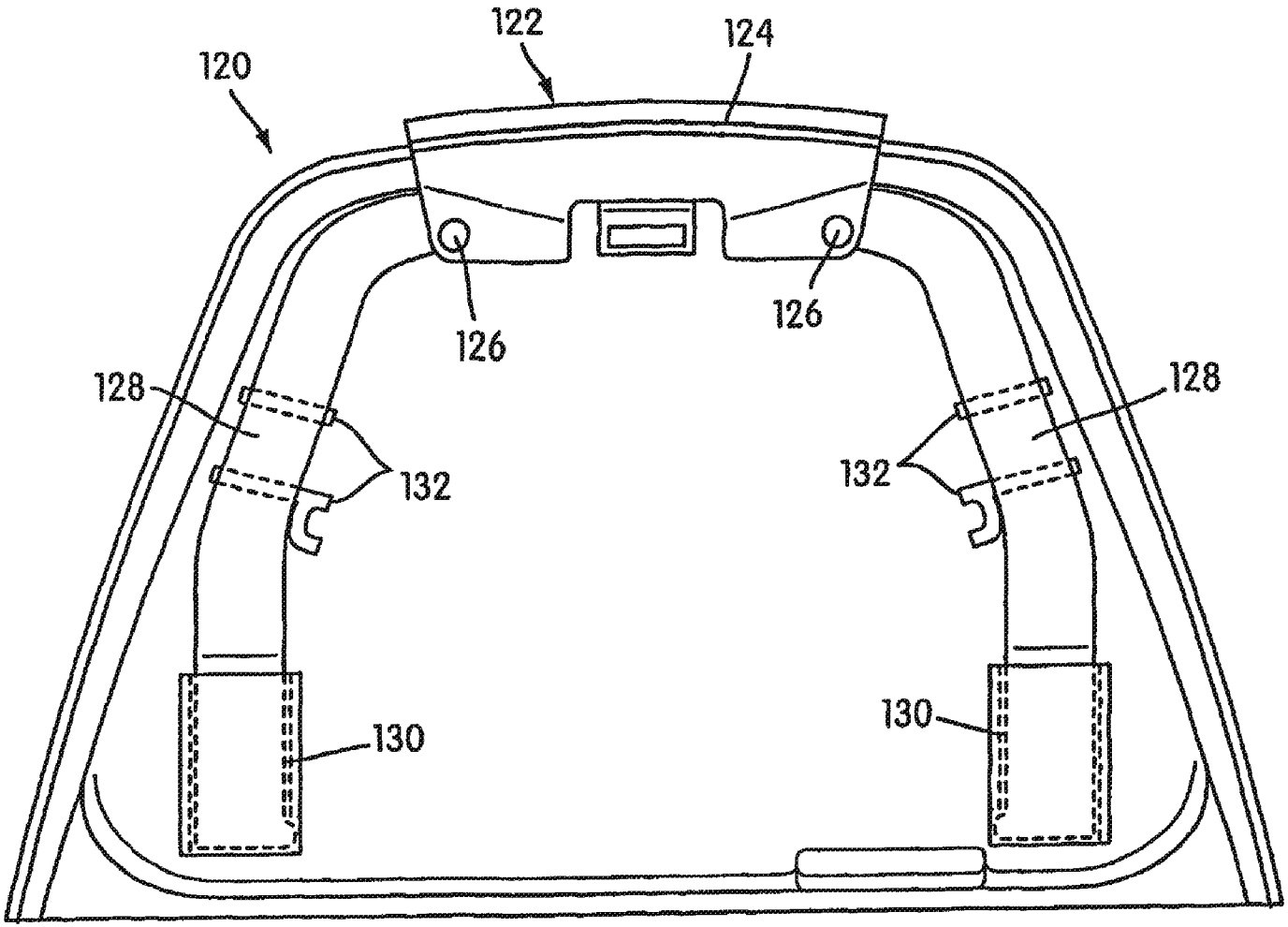
Figure 17:
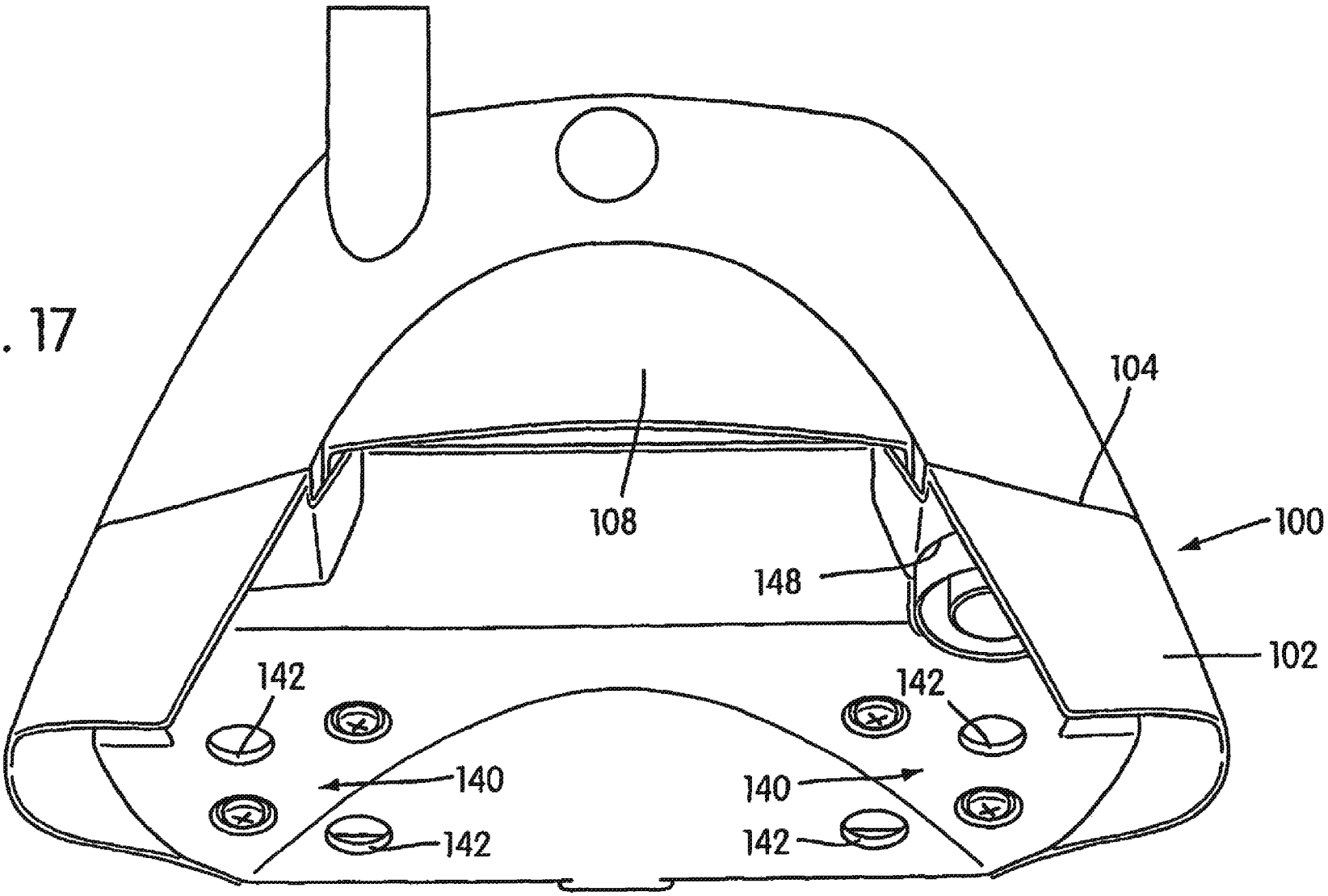
Figure 18:
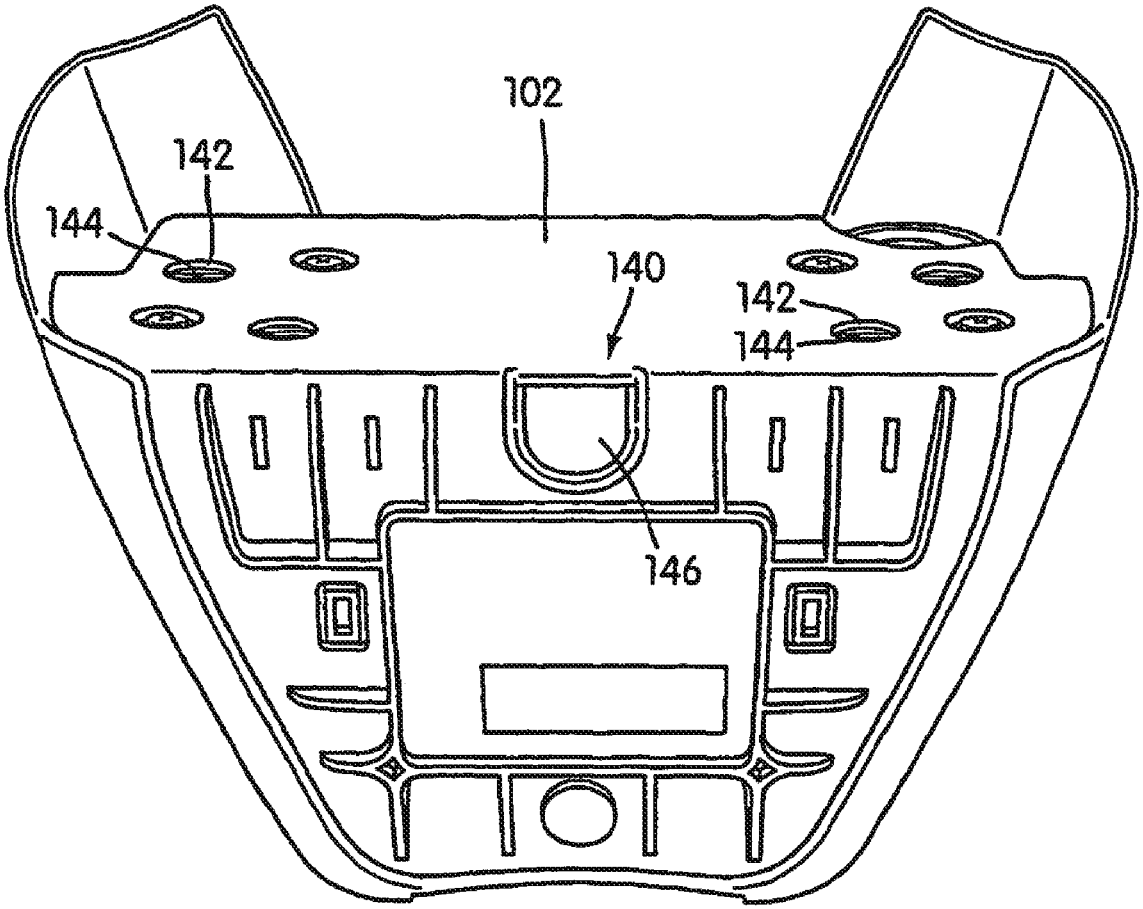
Figure 19:
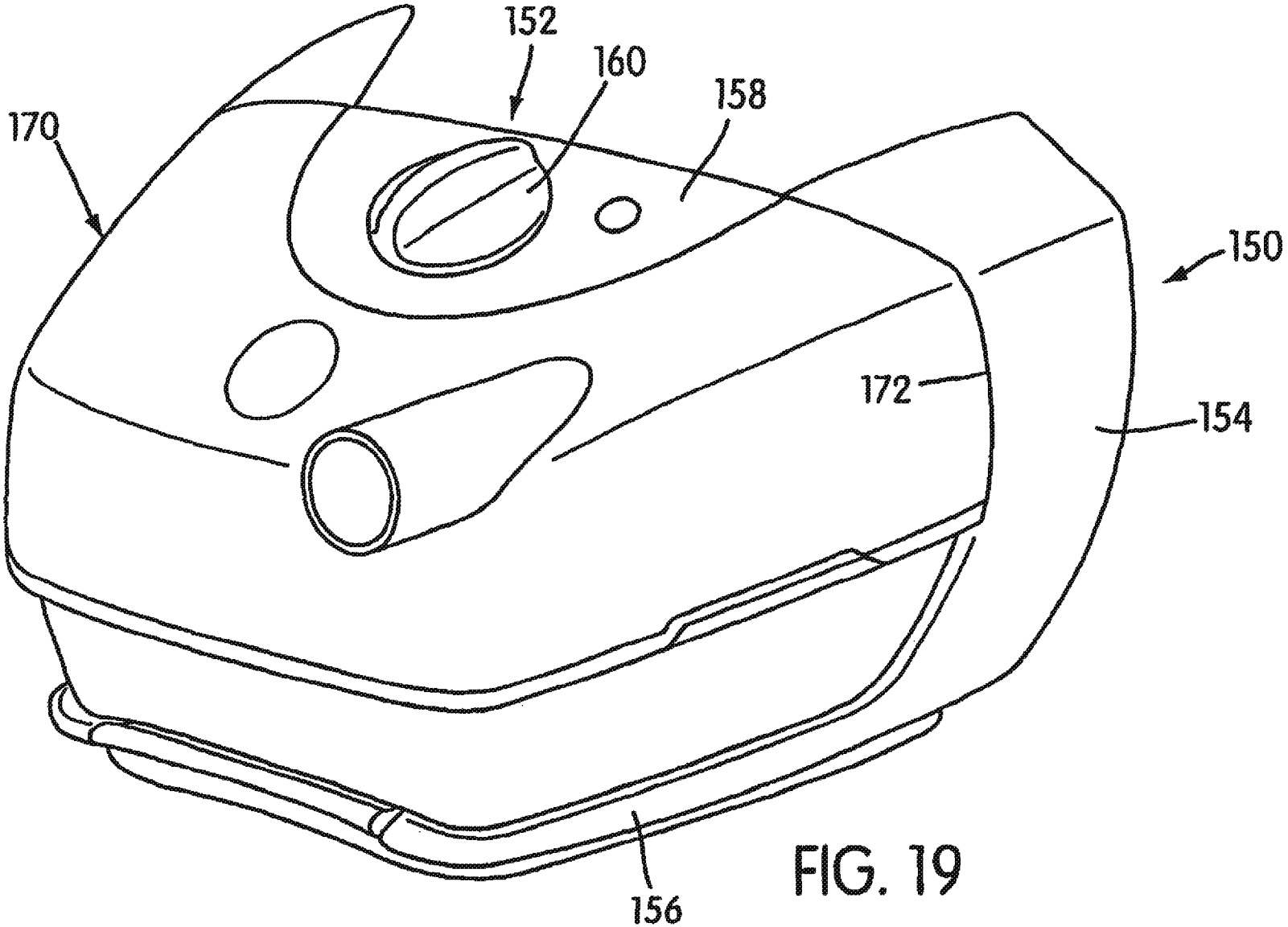
Figure 20:
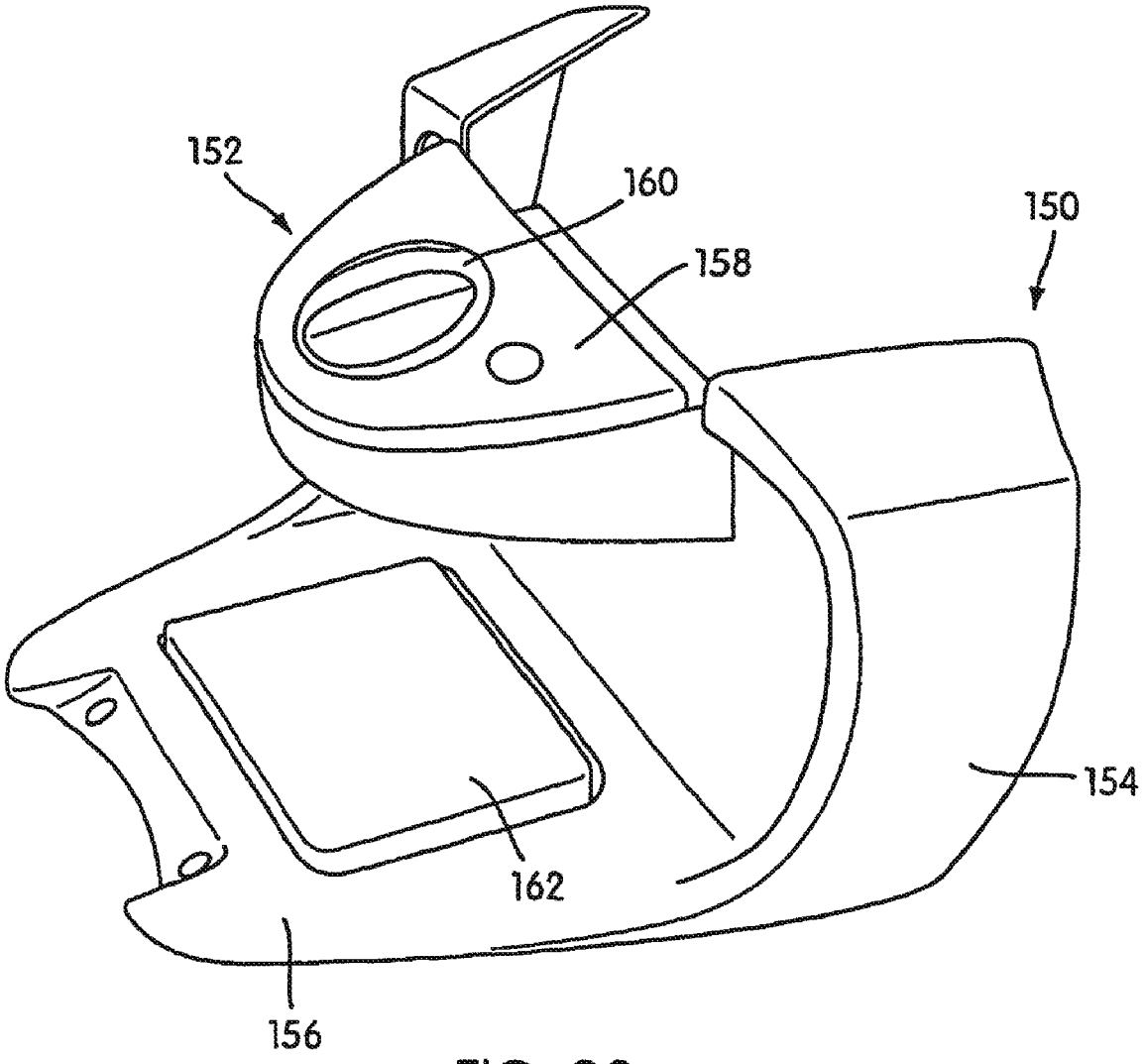
Figure 22:
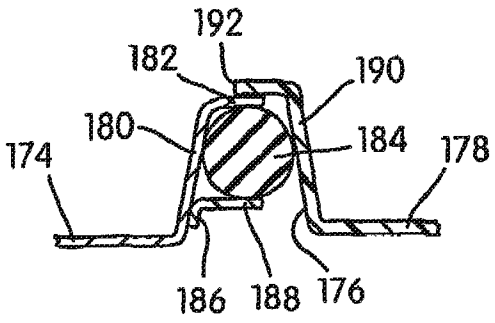
Figure 21:
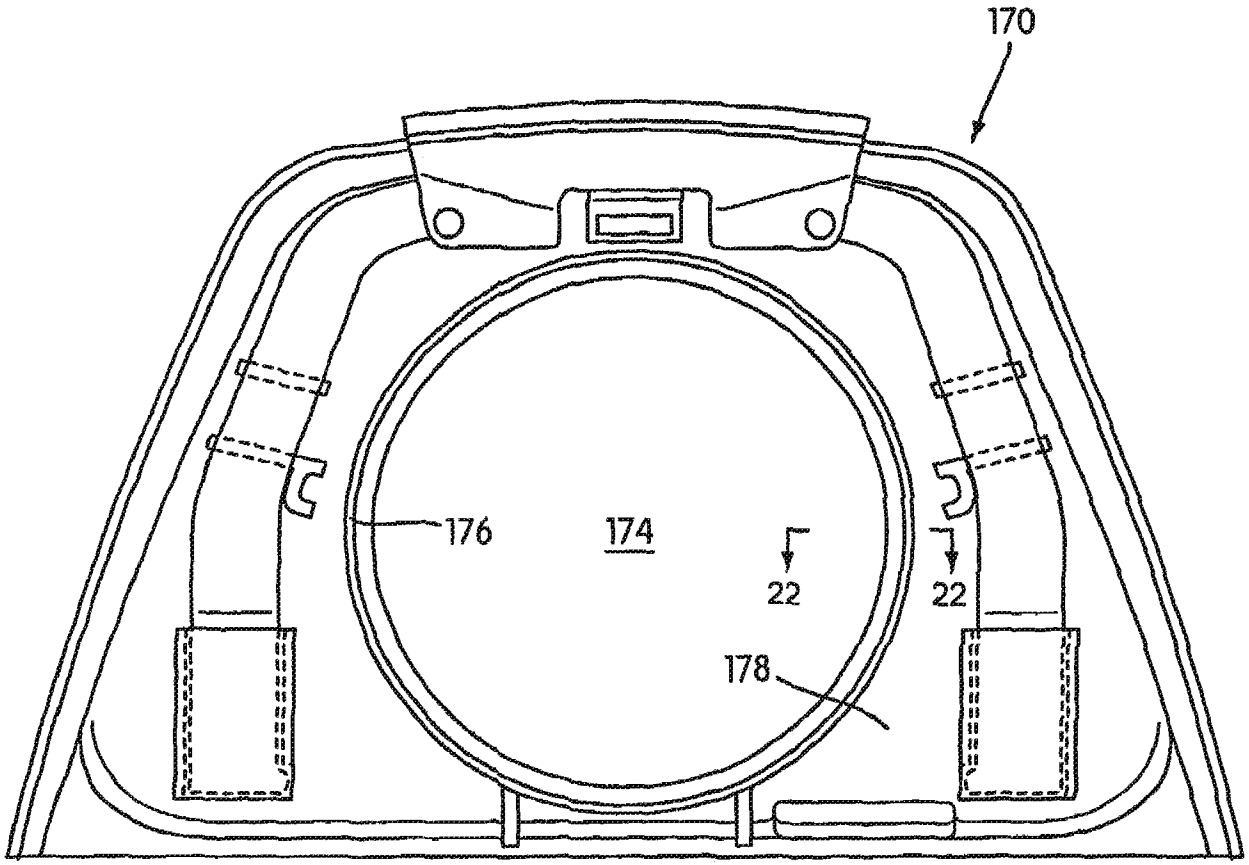
Figure 23:
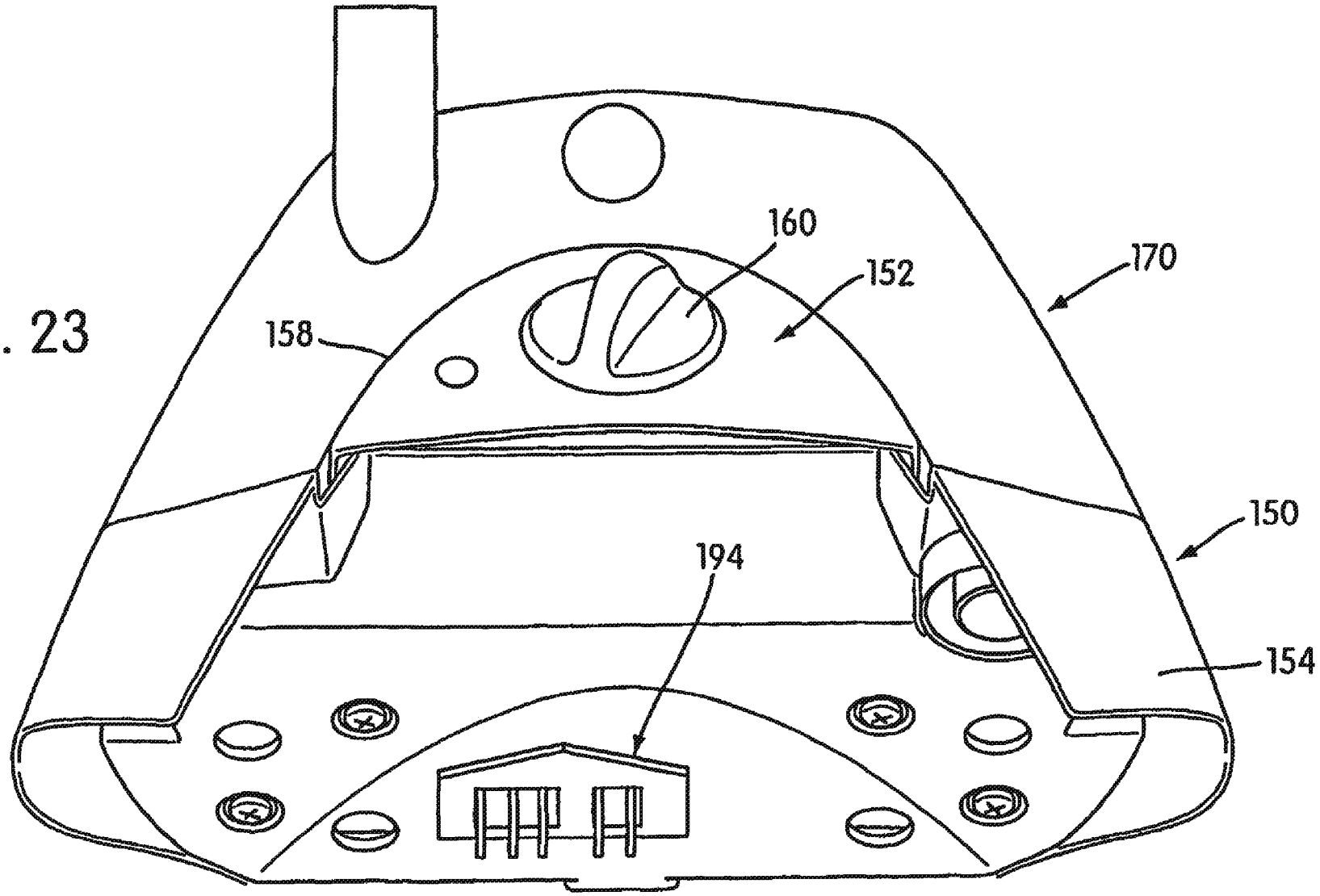

FIG. 7. Is an exploded perspective view of the humidifier shown in FIG. 6;

FIG. 8 is a partial sectional view of the humidifier shown in FIG. 6;

FIG. 9 is schematic view of the humidifier shown in FIG. 6 showing an air flow path through the humidifier;

FIGS. 10-13 are schematic views of the humidifier shown in FIG. 6 in corresponding non-working, upright orientations;

FIG. 14 is a perspective view of a humidifier and connecting structure according to another embodiment of the present invention;

FIG. 15 is a perspective view of the connecting structure shown in FIG. 14;

FIG. 16 is a bottom plan view of the humidifier shown in FIG. 14;

FIG. 17 is a rear perspective view of the humidifier and connecting structure shown in FIG. 14;

FIG. 18 is a bottom perspective view of the connecting structure shown in FIG. 14;

FIG. 19 is a perspective view of a humidifier and heater according to another embodiment of the present invention;

FIG. 20 is a perspective view of the heater shown in FIG. 19;

FIG. 21 is a bottom view of the humidifier shown in FIG. 19;

FIG. 22 is a cross-sectional view taken along line 22-22 in FIG. 21; and FIG. 23 is a rear perspective view of the humidifier and heater shown in FIG. 19.

Figure 1:
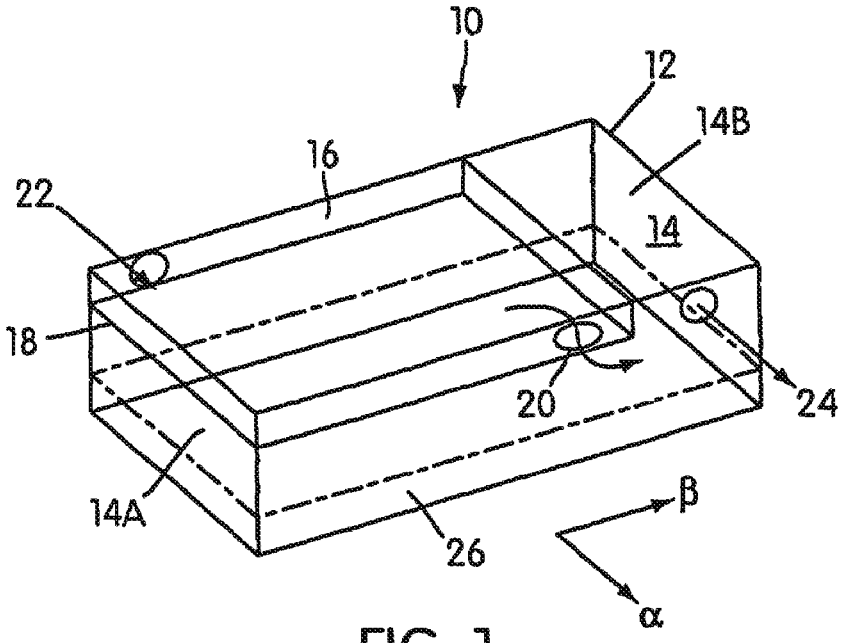
FIG. 1 is a schematic view of a humidifier according to one embodiment of the present invention in a working, upright orientation.

FIG. 1 schematically illustrates one embodiment of the humidifier of the present invention, indicated at 10. The humidifier 10 includes a humidifier body 12 defining a fluid reservoir and fluid passage therein. Additionally, there are two chambers 14, 16 defined by the humidifier body 12 and a dividing member 18. The dividing member 18 includes an orifice 20 therethrough to communicate the chambers 14, 16 to one another. Air from a blower (not shown) arrives in the first chamber 16 via a first chamber inlet 22. Air departs from the second chamber 14 via a second chamber outlet 24. The fluid passage includes the inlet 22, outlet 24, the orifice 20, and, at least, portions of the chambers 14, 16. The humidifier 10 is designed to carry a body of liquid 26 having a maximum volume, $V_{max}$.

In a working orientation represented in FIG. 1, the liquid body 26 lies in a bottom portion of the second chamber 14. With respect to the orientation of the humidifier 10 depicted in FIG. 1, e.g., the orifice 20 lies forward of and to the side of the first chamber inlet 22 (e.g., at a diagonally opposite end of the chamber 16). As shown, the volume of a first portion 14A of the second chamber 14, which lies directly beneath the first chamber 16, is greater than $V_{max}$ due to its relatively increased height. Additionally, the volume of a second portion 14B of the second chamber 14, which is disposed to the side of the first chamber 16, is greater than $V_{max}$. Furthermore, the volume of a portion of the second chamber 14 forward of the inlet 22 plus a portion of the first chamber 16 forward of the inlet 22 is greater than $V_{max}$. Additionally, the volume of a portion of the second chamber 14 to the side of the inlet 22 plus a portion of the first chamber 16 to the side of the inlet 22 is greater than $V_{max}$. Hence, in order to minimize the volume of the humidifier 10, the first chamber inlet 22 is positioned as far to one side of the humidifier body 12 and as far rearward of the humidifier body 12 as possible.

The embodiment of the humidifier 10 shown in FIGS. 1-5 is configured to prevent liquid from the liquid body 26 from exiting through the inlet 22 thereof, such as when inadvertently rotated from an upright, normal working position (generally illustrated in FIG. 1). For this reason, it is preferable for the humidifier 10 to be capable of being rotated from the upright, working position by about 120° without allowing liquid to exit from the inlet 22. It is more preferable for the humidifier 10 to be capable of being rotated from the upright, working position by about 80°-110° without allowing liquid to exit from the inlet 22. It is contemplated that for the embodiment of the humidifier 10 shown in FIG. 1, it may be especially preferable for the humidifier 10 to be capable of being rotated from the upright, working position by about 90° without allowing liquid to exit from the inlet 22, since the humidifier 10 is readily able to be placed on one side thereof due to the substantially flat, normal sides thereof. However, of course, it may be desirable for the humidifier 10 to be capable of being rotated more or less than 90°, depending on the particular configuration of the humidifier 10. It is noted that while the humidifier 10 is designed to prevent liquid from exiting the inlet thereof when inadvertently oriented in other than the upright working position, it may be possible to purposefully enable liquid to exit from the inlet, such as by jostling or rapidly and/or repeatedly rotating the humidifier 10. In situations wherein it is highly undesirable for liquid to exit the inlet of the humidifier, the configuration (e.g., volume) of the chambers, size and placement of the inlet and outlet, and size and placement of the aperture intercommunicating the chambers may be altered from the illustrated embodiment to decrease the possibility of liquid exiting the inlet of the humidifier.

Figure 2:
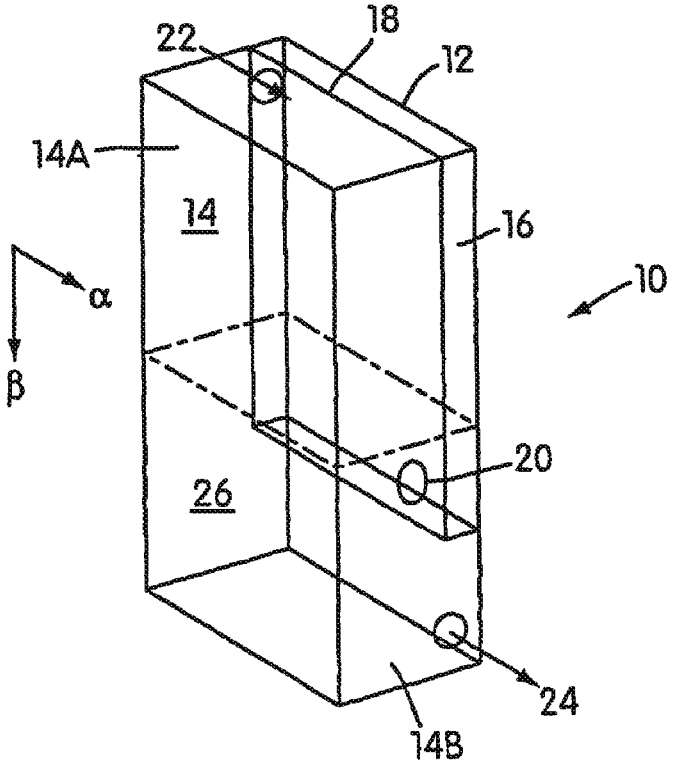
FIGS. 2-5 are schematic views of the humidifier shown in FIG. 1 in corresponding non-working, upright orientations.

As shown in FIG. 2, the arrangement of the chambers 14, 16, inlet 22, and outlet 24 means that, if the humidifier 10 is rotated in a clockwise direction by up to 90° about axis α, then the liquid body 26 will accumulate in the second portion 14B of the second chamber 14 and a portion of the first chamber 16 adjacent the outlet 24. In this situation, liquid of the liquid body 26 may run out of the outlet 24, but will not run out of the inlet 22 back into the blower.

Figure 3:
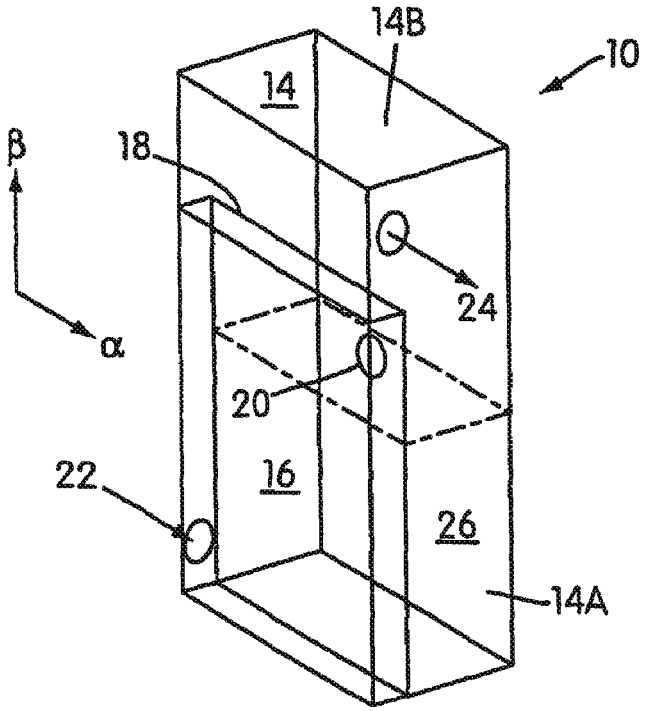

Similarly, as shown in FIG. 3, if the humidifier 10 is rotated in a counter-clockwise direction (relative to the position illustrated in FIG. 1) by up to 90° about axis α, then the liquid body 26 will accumulate in the first portion 14A of the second chamber 14, but will not spill over orifice 20 into the first chamber 16.

Figure 4:
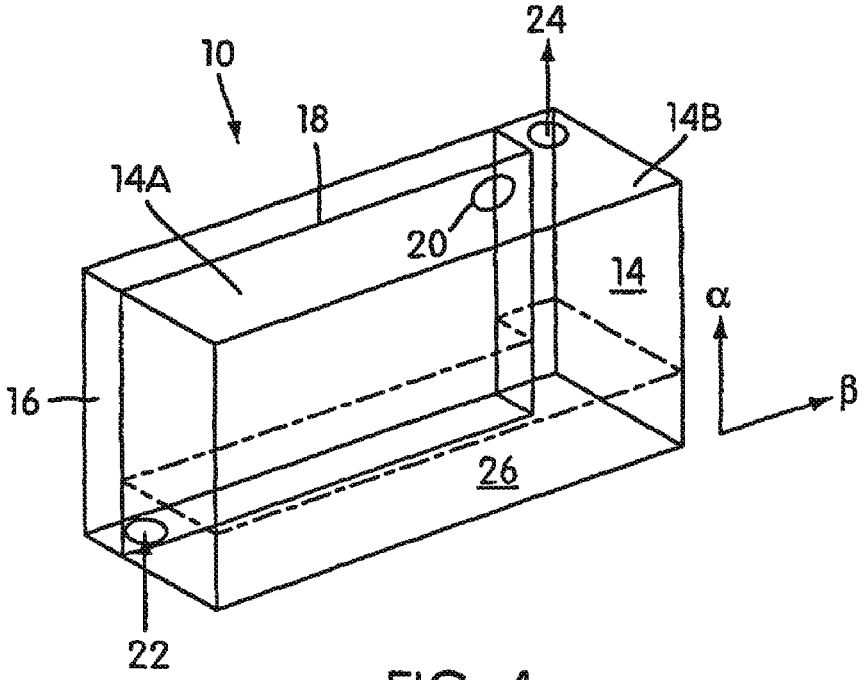

As shown in FIG. 4, if the humidifier 10 is rotated in a clockwise direction (relative to the position illustrated in FIG. 1) up to 90° about axis β, then the liquid body 26 will accumulate in a rearward portion of the second chamber 14 but will not spill over orifice 20 into the first chamber 16.

Figure 5:
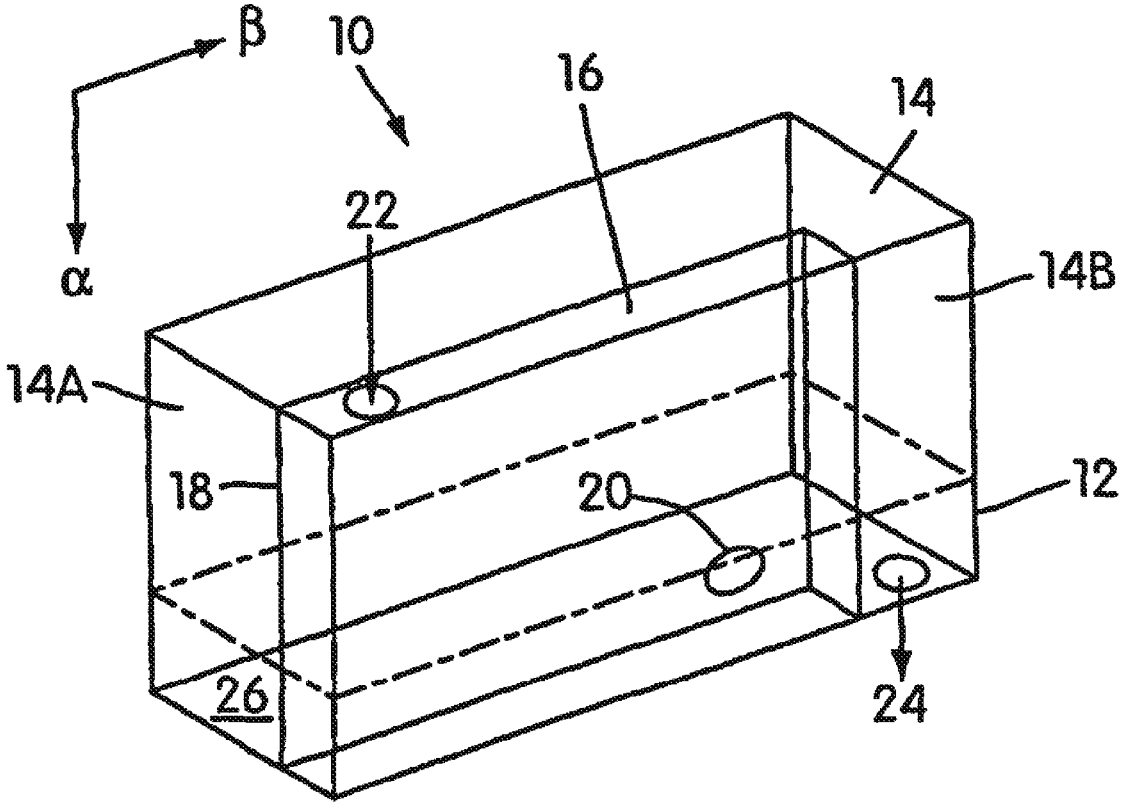

As shown in FIG. 5, if the humidifier 10 is rotated in a counter-clockwise direction (relative to the position illustrated in FIG. 1) up to 90° about axis β, then the liquid body 26 will accumulate in forward portions of the first and second chambers 14, 16 and will not spill back through first chamber inlet 22. Furthermore, liquid of the liquid body 26 will drain out of the humidifier 10 through second chamber outlet 24.

In the embodiment illustrated in FIGS. 1-5, the humidifier 10 has an exterior shape that is generally rectangular and the humidifier 10. As illustrated, the inlet 22 is positioned to correspond to a blower outlet being on the upper left-hand side when viewed from the front in an upright position. Therefore the humidifier inlet 22 is positioned at the back of the humidifier 10 on the upper left-hand side, when viewed from the front in an upright position. The humidifier outlet 24 lies on the front upper right-hand side, when viewed from the front in an upright position. However, it is, of course, possible for the inlet and outlet to be repositioned corresponding to the position of the blower outlet.

For each of the orientations of the humidifier 10 shown in FIGS. 1-5, the level of the liquid body 26 is always below the level of at least one of the inlet 22 and orifice 20 intercommunicating the first and second chambers 16, 14. In this manner, in a case wherein the inlet 22 is disposed below the level of the liquid body 26 (such as in orientations illustrated in FIGS. 3 and 4), the orifice 20 is disposed above the level of the liquid body 26, which prevents liquid from flowing therethrough and exiting the inlet 22. Conversely, in a case wherein the orifice 20 is disposed-below the level of the liquid body 26 (such as in orientations illustrated in FIGS. 2 and 5), the inlet 22 is disposed above the level of the liquid body 26. Accordingly, liquid may flow through the orifice 20, but is prevented from exiting through the inlet 22.

FIG. 6 shows another embodiment of a humidifier 30 according to the present invention. The humidifier 30 includes an inlet 32 and an outlet 34, both of which are communicated with an interior of the humidifier 30. The interior of the humidifier 30 defines a reservoir for a body of liquid and a fluid passage. The fluid passage is communicated to each of the inlet 32 and outlet 34 and is configured such that fluid (e.g., breathable gas at an elevated pressure) flowing therethrough is exposed to the body of liquid. Additionally, the humidifier 30 is adapted for detachable connection to an NIPPV or CPAP apparatus (not shown) which includes a blower. When connected, the output of the blower is attached to the inlet 32. Air from the blower enters the inlet 32, flows through the fluid passage, and collects moisture through contact with the liquid body, before continuing on to the outlet 34 and then to the patient.

It is also contemplated that the humidifier 30 may include an additional internal passage to allow monitoring of the CPAP pressure without degrading signal strength or necessitating relatively large correction factors due to signal attenuation within the humidifier, such as described in co-pending Applications incorporated above, as well as co-pending Application No. WO 02/066107, entitled "Air Pressure Signal Monitoring in Apparatus for Treating Sleep Disordered Breathing", filed on even date herewith and hereby incorporated by reference in its entirety.

As shown in FIG. 7, the humidifier 30 includes a top cover 36, a gasket 38, and a base 40. The gasket 38 is disposed between the top cover 36 and base 40, which are secured together via sliding clips 72. (See FIG. 6.) Of course, other suitable fastening arrangements and constructions are possible. For example, the top cover 36 and base 40 may be formed with snap-fit or other cooperating constructions. Alternatively, other types of mechanical fasteners may be utilized. It is contemplated that the top cover 36 may be formed from a relatively rigid polymer material, such as polysulfone (for example, grade UDEL P1700, manufactured by BP Amoco Polymers), and includes the inlet 32 and the outlet 34. The gasket 38 may be formed from a relatively resilient material, such as silicone rubber (for example, SILASTIC 94595-IIC, manufactured by Dow Corning) and is divided into first and second sections 42 and 44 by a channel structure 46. The first section 42 includes a raised portion 48 having a first aperture 50 extending vertically therethrough. The second section 44 includes a plurality of second apertures 52 extending vertically therethrough and being separated from one another by ribs 54. The top cover 36 may also include a divider wall structure 56 (FIG. 8) which corresponds to and is received within the channel structure 46 of the gasket 38. The gasket 38 includes a sealing flange 58 formed about a periphery thereof. The base 40 may be formed from the same or similar rigid polymer material as the top cover 36 and may include a receptacle 60 formed therewithin, a bottom portion 62, and side walls 64 extending upwardly from the bottom portion 62. The base 40 may also include a removable bridge structure 66, which divides the receptacle 60 into two sections 68 and 70, which correspond to the sections [22] *42* and [24] *44* of the gasket 38.

As shown in FIG. 8, to assemble the humidifier 30, the gasket 38 is attached the base 40. The flange 58 of the gasket 38 forms a sealing engagement with an upper edge portion of the side walls 64 of the base 40. The top cover 36 is then attached to the base 40 via sliding clips 72 (FIG. 6) on opposite sides of the humidifier 30, such that the top cover 36 covers and seals with the gasket 38. The removable bridge structure 66 vertically supports an intermediate portion of the gasket 38. As shown, a downwardly facing surface of the channel structure 46 of the gasket 38 engages an upwardly facing surface of the bridge structure 66. When assembled, the gasket first section 42, the top cover 36, and the divider wall structure of the top cover 36 together form a first chamber 74. The receptacle 60 of the base 40 together with the gasket 38 form a second chamber 76. The first chamber 74 is thus located above the second chamber 76 and the volume of the second chamber 76 is larger than the volume of the first chamber 74. The first and second chambers 74, 76 are in communication with one another via the first aperture 50 within the gasket 38. The second chamber 76 is in communication with the outlet 34 via the second apertures 52 within the gasket 38.

In use, a predetermined maximum volume of liquid is poured into the receptacle 60 of the base 40 after removing the top cover 36 and the sealing gasket 38 from the base 40. The top cover 36 and the sealing gasket 38 are then reattached to the base 40. As shown in FIG. 9, a body of liquid 78 is held in the second chamber 76 when the humidifier 10 is in the upright working orientation of the humidifier 30. Breathable gas from the blower enters the inlet 32 and travels through the first chamber 74 and into the first aperture 50. The gas passes through the aperture 50 and enters the second chamber 76 where it is humidified by contact with the body of liquid 78, before exiting through apertures 52 in the gasket 38, and then out through outlet 34 (FIG. 6).

In the working upright orientation of the humidifier 30, as shown in FIG. 9, a liquid level, indicated at 81, of the body of liquid 78 is below the aperture 50. Thus, liquid from the body of liquid 78 cannot exit via the inlet 32 and there is no risk of damaging the electronic components of the NIPPV or CPAP apparatus. The body of liquid 78, however, will be displaced in the humidifier 30 according to the orientation of the humidifier 30. Accordingly, the humidifier 30 is configured to substantially prevent liquid of the body of liquid 78 from exiting through the inlet 32 in non-upright orientations to avoid damage to the NIPPV or CPAP apparatus connected to the humidifier 30.

Similarly as with the embodiment illustrated in FIGS. 1-5, the embodiment of the humidifier 30 shown in FIGS. 6-13 is configured to prevent liquid from the liquid body 78 from exiting through the inlet 32 thereof, such as when inadvertently rotated from an upright normal working position (generally illustrated in FIG. 6). For this reason, it is preferable for the humidifier 30 to be capable of being rotated from the upright, working position by about 120° without allowing liquid to exit from the inlet 32. It is more preferable for the humidifier 30 to be capable of being rotated from the upright, working position by about 80°-110° without allowing liquid to exit from the inlet 32. It may be especially preferable for the humidifier 30 to be capable of being rotated from the upright, working position by about 90° without allowing liquid to exit from the inlet 32. However, of course, it may be desirable for the humidifier 30 to be capable of being rotated more or less than 90°. It is noted that while the humidifier 30 is designed to prevent liquid from exiting the inlet thereof when inadvertently oriented in other than the upright working position, it may be possible to purposefully enable liquid to exit from the inlet, such as by jostling or rapidly and/or repeatedly rotating the humidifier 30. In situations wherein it is highly undesirable for liquid to exit the inlet of the humidifier, the configuration (e.g., volume) of the chambers, size and placement of the inlet and outlet, and size and placement of the aperture intercommunicating the chambers may be altered from the illustrated embodiment to decrease the possibility of liquid exiting the inlet of the humidifier.

For each of the orientations of the humidifier 30 shown in FIGS. 10-13, the level of the liquid body 78 is always below the level of at least one of the inlet 32 and aperture 50 intercommunicating the first and second chambers 74, 76. In this manner, in a case wherein the inlet 32 is disposed below the level of the liquid body 78 (such as in orientations illustrated in FIGS. 10 and 12), the aperture 50 is disposed above the level of the liquid body 78, which prevents liquid from flowing therethrough and exiting the inlet 32. Conversely, in a case wherein the aperture 50 is disposed below the level of the liquid body 78 (such as in orientations illustrated in FIGS. 11 and 13), the inlet 32 is disposed above the level of the liquid body 78. Accordingly, liquid may flow through the aperture 50, but is prevented from exiting through the inlet 32.

Figure 10:
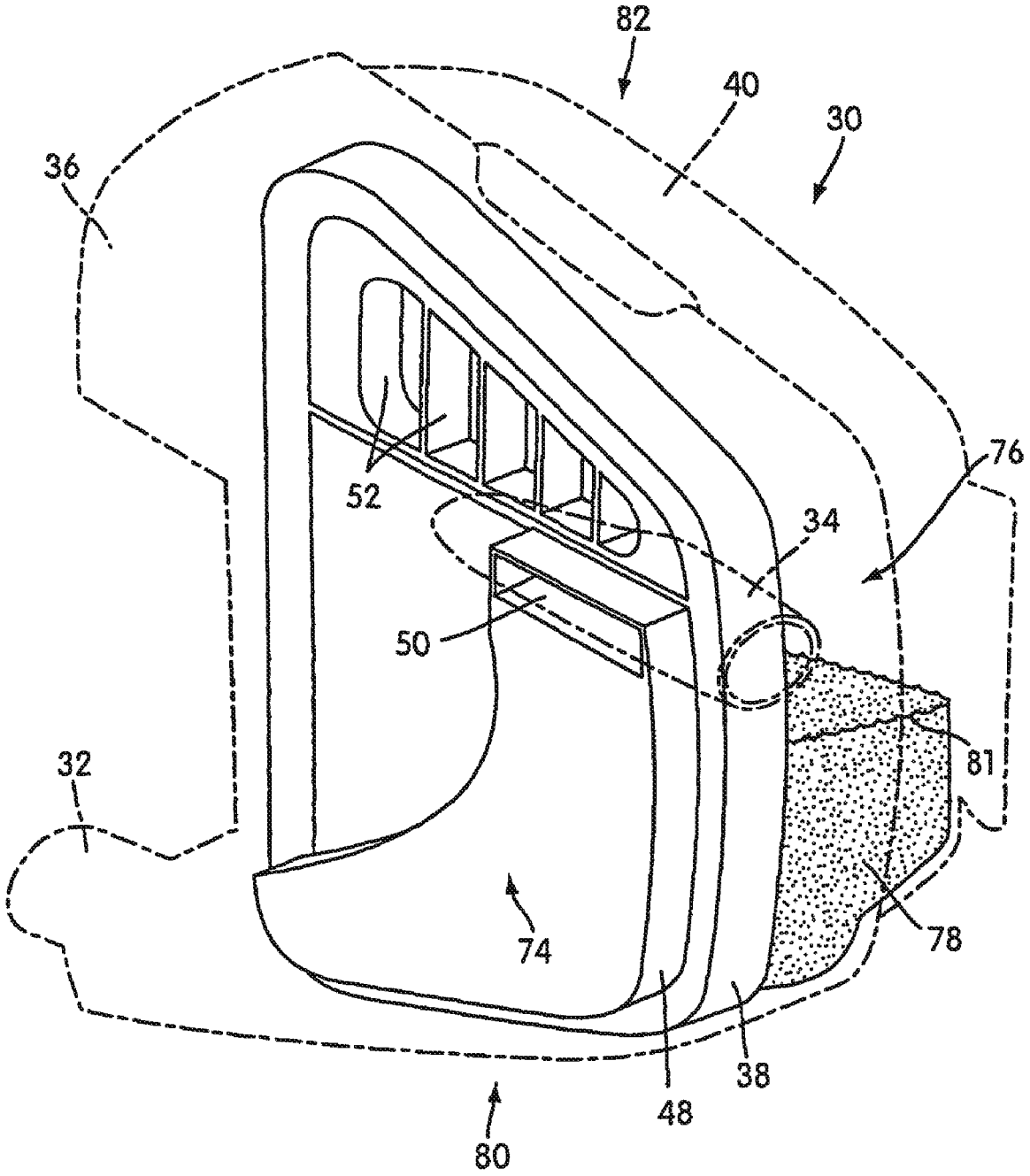

In FIG. 10, the humidifier 30 is rotated to an angle about 90° from the working upright orientation, such that a side 80 thereof corresponding to the side of the humidifier 30 adjacent the inlet 32, is oriented below a side 82 thereof corresponding to the side of the humidifier 30 adjacent the outlet 34. Because the raised portion 48 of the gasket 38 increases the volume of the second chamber 76, the body of liquid 78 remains only in the second chamber 76 and the level 81 of the liquid body 78 remains below the first aperture 50. Thus, the liquid will not exit through the inlet 32.

Figure 11:
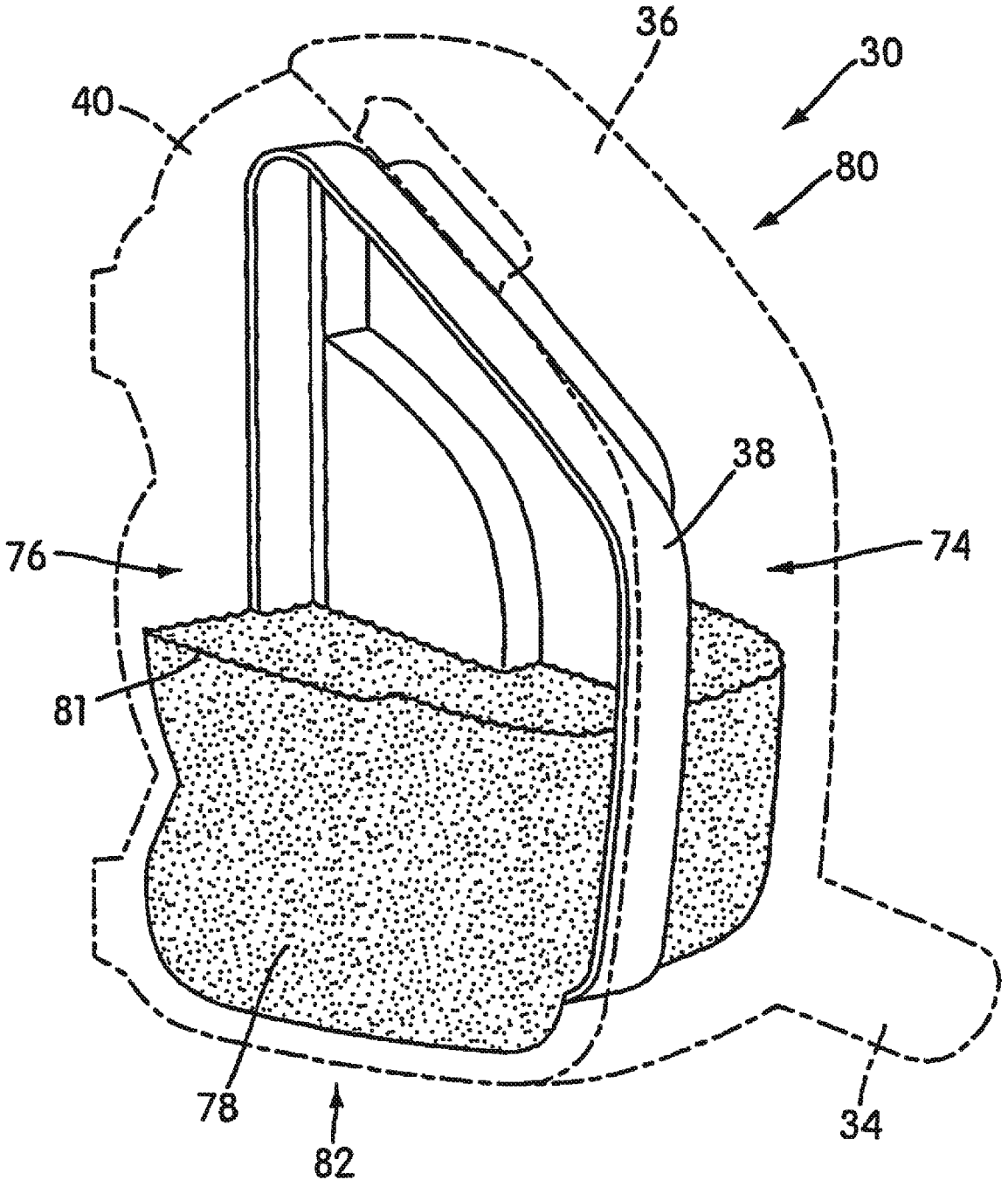

In FIG. 11, the humidifier 30 is rotated to an angle about 90° from the working upright orientation, such that the side 82 is below the side 80 (i.e., flipped 180° from the orientation illustrated in FIG. 11). As the level 81 of the body of liquid 78 is above (at least initially) the apertures 52, liquid will pass therethrough and exit the outlet 34. However, since the level 81 of the liquid body 78 is below the inlet 32, liquid will not exit through the inlet 32. Liquid exiting through the outlet 34 is generally acceptable as there is not generally a risk in damaging the NIPPV or CPAP apparatus.

Figure 12:
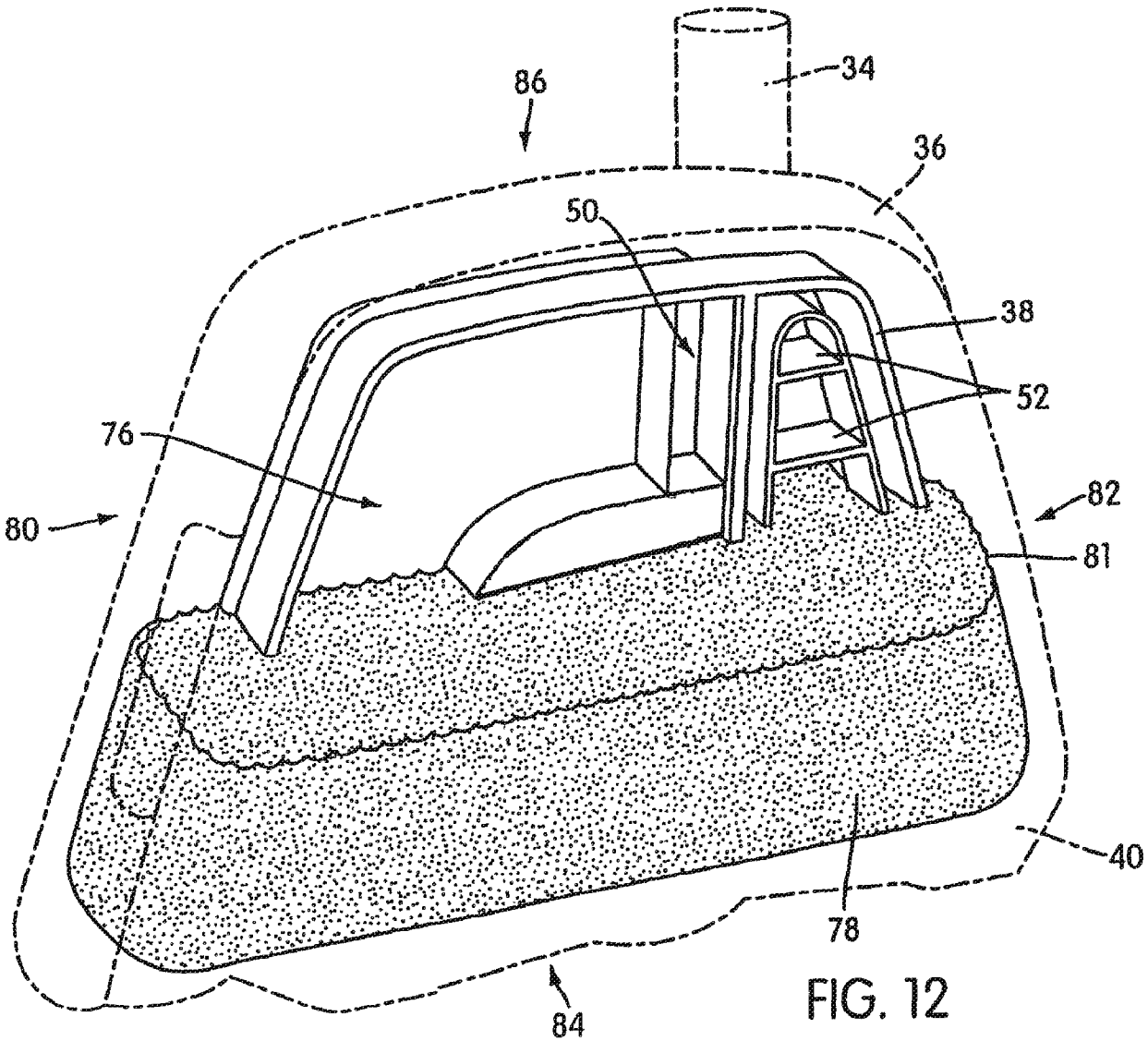

In FIG. 12, the humidifier 30 is rotated to an angle about 90° from the working upright orientation, such that a rear side thereof indicated at 84, corresponding to the side at which the inlet 32 is located, is below a forward side thereof indicated at 86, corresponding to the side at which the outlet 34 is located. As shown, the body of liquid 78 remains substantially in the second chamber 76 and the level 81 of the liquid body 78 remains below the first aperture 50. Thus, water cannot exit through the inlet 32.

Figure 13:
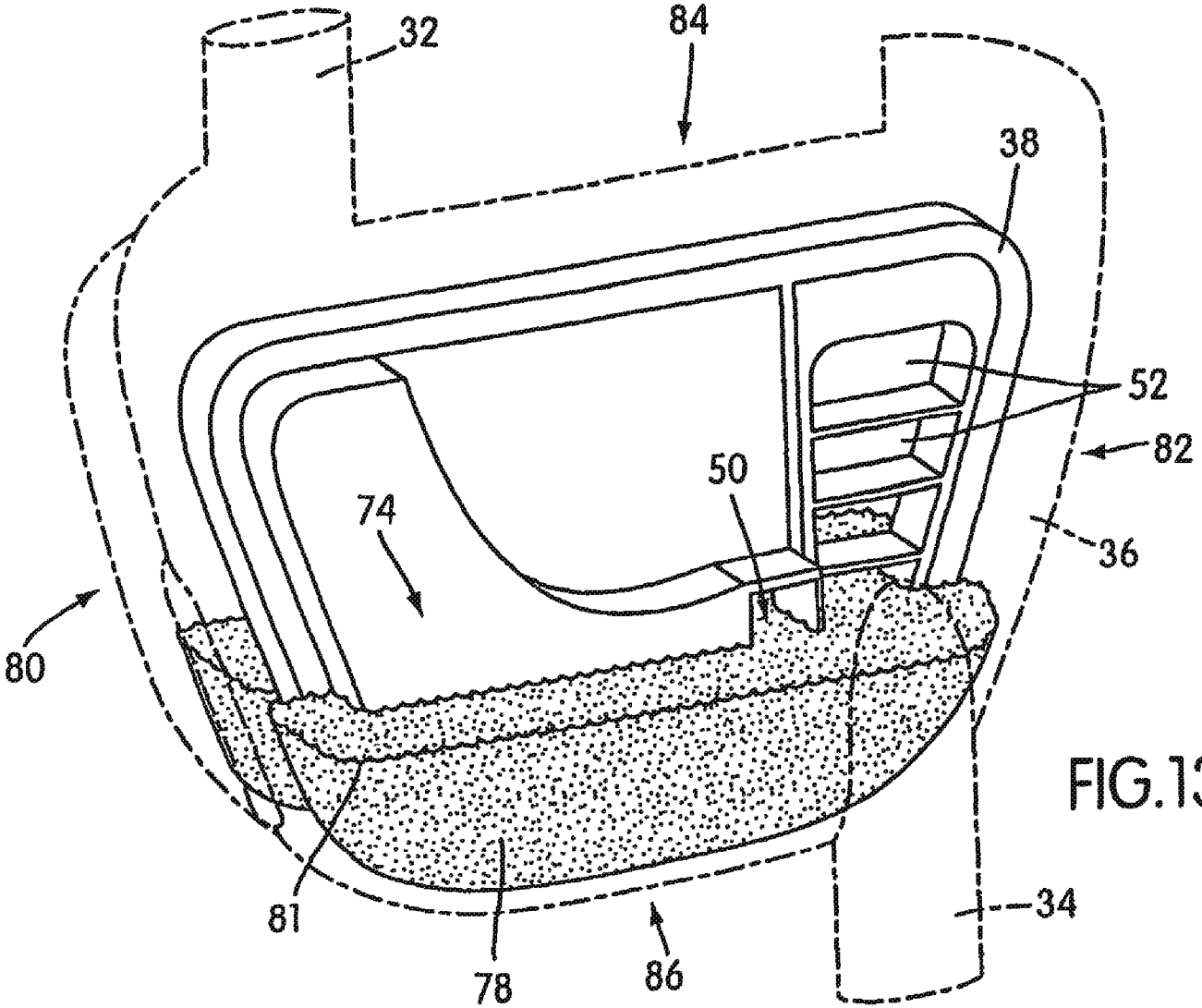

FIG. 13 illustrates when the humidifier 30 is tilted to an angle about 90° from the working upright orientation, such that the forward side 86 is below the rear side 84. As shown, the body of liquid 78 is disposed within forward portions of the first and second chambers 74, 76. As the level 81 of the body of liquid 78 is at least initially above the level of the aperture 50, liquid will flow through the aperture 50 into the first chamber 74. However, since the inlet 32 is disposed above the level of the body of liquid 78 in this orientation, no liquid exits through the inlet 34.

The humidifier 30 thus ensures that the body of liquid 78 is disposed in one of (a) only the second chamber 76, or (b) portions of the first and second chambers 74, 76 at a level below the inlet 32, to prevent liquid from exiting through the inlet 32 at orientations of the humidifier 30 up to an angle of about 90° from the working upright orientation. In the illustrated embodiment, a number of features of the humidifier 30 contribute to ensuing this function. These include relive positions of the inlet 32 and first aperture 50. More particularly, the inlet 32 and first aperture 50 are located on opposing ends of the first chamber 74. Also, the volume of the second chamber 76 is larger than the volume of the first chamber 74, which is assisted by the raised portion 48 of the gasket 38 so that liquid displaced from the first chamber 74 may be accommodated within the second chamber 76 without overflow through aperture 50. Furthermore, the outlet 34 is located closer to the first aperture 50 than the inlet 32, which assists in ensuing that liquid will exit via the outlet 34, rather than though the inlet 32.

The humidifier 30 therefore substantially prevents or reduces the risk of water exiting through the inlet 32, which may damage the NIPPV or CPAP apparatus, when the humidifier 30 is in other orientations up to an angle of about 90° from its working upright orientation.

It is contemplated that the humidifier 30 may be used as a retrofit or add-on component for a CPAP apparatus. To facilitate this usage, it may be preferable to provide a connecting structure 100 that is configured to connect between the CPAP apparatus and humidifier 30. As shown in FIGS. 14 and 15, the connecting structure 100 includes a housing 102, which provides a generally horizontally extending receptacle 104 within which the humidifier 30 may be disposed. The housing 102 provides a base portion 106 that is configured to support the humidifier 310 thereon and a retaining portion 108 configured to secure the humidifier 30 in position. As shown in FIG. 16, the retaining portion 108 extends generally parallel to the base portion 106 and is spaced above the base portion 106. Referring back to FIG. 14, the humidifier 30 may be formed with a recess 110 that is open and of a complimentary shape to receive the retaining portion 108 therein.

To facilitate connection of the humidifier 30 to the connecting strut 100, it is contemplated that another embodiment of a humidifier, indicated at 120 in FIG. 16, may include a securing mechanism 122. As shown, the securing mechanism 122 includes a resiliently biased pull member 124 that includes one or more locking lugs 126 extending generally downwardly therefrom. The pull member 124 is disposed at a forward end (assuming the rearward end of the humidifier 120 is adjacent the connecting structure 100) of the humidifier 120 and is resiliently biased by a pair of resilient legs 128. Rearward portions of the legs 128 are relatively securely retained within corresponding pocket structures 130 provided on a bottom side of the humidifier 120. Ribs 132 extend is downwardly from the bottom side of the humidifier 120 and engage an intermediary portion of the legs 128 to define a space between the resilient legs 128 and the bottom side of the humidifier 120. In this manner, the pull member 124 is biased generally downwardly by the resilient legs 128, but may be manually moved (e.g., pulled) upward against a resilient bias of the legs 128.

As shown in FIG. 15, a forward portion of the base portion 106 includes generally upwardly open lug receiving recesses 134 within which the lugs 126 may be disposed when the humidifier 120 is disposed within the receptacle 104. As the humidifier 120 is inserted within receptacle 104, the legs 128 resiliently bias the legs 126 into recesses 134. The lugs 126 and recesses 134 thereby secure the humidifier 120 within the receptacle 104. To remove the humidifier 120 from the receptacle 104, the pull member 124 is pulled upwardly to withdraw the lugs 126 from the recesses 134. The humidifier 120 may then be pulled generally horizontally out of the receptacle 104.

FIG. 17 shows a rearward side of the connecting structure 100. The rearward side of the connecting structure 100 provides a retaining mechanism 140 to secure the connecting structure 100 to the CPAP apparatus. It is contemplated that the retaining mechanism 140 may include a series of apertures 142 within the rearward portion of the housing 102. The apertures 142 may receive therein, for example, prongs or tabs (not shown) provided by the CPAP apparatus. As shown in FIG. 18, within each aperture 142, a locking member 144 may be provided that is resiliently biased toward a position that partially encloses the respective aperture 142. As also shown in FIG. 18, a button structure 146 may be coupled to the locking members 144, such that manual movement of the button structure 146 moves the locking members 144 out of their biased positions to substantially fully open the apertures 142. It is contemplated that the tabs or prongs on the CPAP apparatus are provided with a groove therein such that when positioned within the apertures 142, the locking members 144 engage within respective grooves to thereby securely and detachably retain the connecting structure 100 to the CPAP apparatus.

Referring back to FIG. 17, the housing 102 of the connecting structure 100 may be provided with an opening 148 that allows the inlet of the humidifier to extend therethrough so as to be connected to the CPAP apparatus.

In certain circumstances, it may be desirable to provide heated humid air to the respirator mask. Accordingly, another embodiment of the connecting structure, indicated at 150 in is FIG. 19, may include a heater 152. The connecting structure 150 may include a housing 154, which provides a base portion 156 and retaining portion 158, similar to the housing 102 described above. As shown in FIG. 19, the retaining portion 158 may include a controller such as a knob or other selecting device 160 thereon to control a heat setting of the heater 152. It is also contemplated that the controller 160 may include a display device, such as an LCD screen.

As shown in FIG. 20, the base portion 156 may include a heating element 162 thereon. The heating element 162 may be in the form of a substantially flat plate-like resistance heater, which heat generated thereby may be directly controlled by the controller 160. As shown in FIG. 19, another embodiment of the humidifier is indicated at 170. The humidifier 170 is disposed within a receptacle 172 provided by the housing 154. It is contemplated that the humidifier 170 has the same basic construction as the humidifiers 10 and 120 described above. However, it is contemplated that the humidifier 170 may include a heating plate 174 (also referred to as a metallic cap) to facilitate heating of the liquid contained therein. In particular, an opening 176 is provided within a bottom wall 178 of the humidifier 170. The heating plate 174 is shaped to fit within the opening 176, as shown in FIG. 21. As shown in more detail in FIG. 22, the heating plate 174 includes an upstanding peripheral wall 180 which includes an outwardly extending peripheral lip 182. A resilient seal member 184 is disposed about an outer periphery of the peripheral wall 180 in contact with the peripheral lip 182. A ring-like retaining member 186 may be press-fit onto the peripheral wall 180 to retain the seal 184 in position on the peripheral wall 180. The retaining member 186 includes an outwardly extending flange structure 188. The seal 184 is disposed between the peripheral lip 182 and flange structure 188. It is contemplated that the retaining member 186 may be press fit onto the heating plate 174, as described above, or may be formed in one piece therewith. The bottom wall 178 of the humidifier 170 is formed with an annular upstanding flange 190 which receives the heating plate 174. It is contemplated that the flange 190 may be slightly tapered inwardly in the upward direction to ease insertion of the heating plate 174. As shown, the flange 190 may include a generally horizontally extending lip structure 192 that vertically retains the heating plate 174.

Referring to FIG. 19, with the humidifier 170 in position within the receptacle 172, a bottom surface of the heating plate 174 is in contact with an upper surface of the heating element 162. In this manner, a heat generated by the heating element 162 is conducively transferred to the heating plate 174. The liquid within the humidifier 170 is exposed to an upper surface of the heating plate 174 and conducts heat therefrom. It is contemplated that a temperature of the liquid within the humidifier 170 may be controlled by manipulation of the controller 160.

It is also contemplated that the heating element 162 may be upwardly resiliently biased to ensure adequate contact between the heating element 162 and the heating plate 174.

As shown in FIG. 23, a rearward portion of the connecting suture 150 may include a plurality of generally outwardly extending contact elements 194. It is contemplated that the contact element 194 may communicate with a power supply within the CPAP apparatus and/or a controller and/or sensors. In this manner, power may be delivered to the heater 152 directly from the CPAP apparatus. Additionally, a controller within the CPAP apparatus itself may control the heater 152. Furthermore, it is contemplated that sensors within the CPAP apparatus may monitor a heat output of the heater 152. Moreover, it may be possible for a CPAP apparatus to automatically adjust a heat output of the heater 152 based on a measured temperature thereof or of the water within the humidifier or of the breathable air exiting the humidifier.

The invention claimed is:

[1. A humidifier assembly for a CPAP apparatus, comprising a humidifier including a base configured to retain a body of liquid therein, at least a portion of the base being constructed of a heat conducting material, a top cover, and a seal disposed between the top cover and the base; and a connecting structure configured to connect between the CPAP apparatus and humidifier and allow communication of an outlet of the CPAP apparatus with the inlet of the humidifier, the connecting structure including a housing providing a base portion to support the humidifier thereon, and a retaining mechanism configured to secure the connecting structure to the CPAP apparatus, wherein the base portion includes a heating element in contact with the heat conducting material of the base of the humidifier.]

[2. A humidifier assembly according to claim 1, wherein the top cover defines both an inlet and an outlet communicated with an interior of the base, the inlet configured to receive pressurized breathable gas and the outlet configured to deliver the pressurized breathable gas with added humidity.]

[3. A humidifier assembly according to claim 1, wherein the connecting structure includes a control knob to control a heat setting of the heating element.]

[4. A humidifier assembly according to claim 1, wherein the connecting structure includes contact elements that communicate with a power supply within the CPAP apparatus.]

[5. A humidifier assembly according to claim 1, wherein the connecting structure is configured to allow removable attachment of the CPAP apparatus to the humidifier.]

[6. A humidifier assembly according to claim 1, wherein the heat conducting material is a metallic material.]

[7. A CPAP apparatus including a humidifier assembly according to claim 1.]

*8. A humidifier for humidifying a flow of pressurized breathable gas to be delivered to a patient, the humidifier comprising:*

*a top cover, a base and a gasket that seals the top cover and the base, the top cover being connected to the base via a snap-fit fastener, the top cover including a humidifier inlet and a humidifier outlet, the base configured to contain water when the humidifier is oriented in an upright, operating position;*

*the humidifier inlet being configured to receive a flow of pressurized breathable gas in a horizontal direction in the upright, operating position;*

*the humidifier outlet being configured to deliver the flow of pressurized breathable gas in a horizontal direction in the upright, operating position;*

*the base comprising a bottom with a heat conducting metallic material configured to contact a heating element to heat the water;*

*wherein the humidifier is configured to direct the flow of pressurized breathable gas downwards into the base to humidify the flow of pressurized breathable gas, and further configured to direct the flow of pressurized*

*breathable gas upwards from the base for delivery through the humidifier outlet,*

*wherein the top cover includes a gas introduction chamber adapted to receive the flow of pressurized breathable gas from the humidifier inlet, the gas introduction chamber extending along a substantially lateral direction and into the humidifier;*

*wherein the humidifier further includes a humidification chamber in communication with the gas introduction chamber and the humidifier outlet, the humidification chamber comprising a bottom portion below the gas introduction chamber when the humidifier is in the upright, operating position, and a side portion beside the gas introduction chamber when the humidifier is in the upright, operating position, and*

*wherein a continuous upper wall of the top cover forms an upper boundary of both the gas introduction chamber and at least the side portion of the humidification chamber.*

*9. The humidifier according to claim 8, further configured so that the humidifier inlet and the humidifier outlet are positioned above the water when the base retains a predetermined maximum volume of water and the humidifier is in the upright, operating position, and wherein the gas introduction chamber and the humidification chamber are configured so that when the base retains the predetermined maximum volume of water and the humidifier is rotated around a horizontal axis parallel to a bottom surface of the humidifier, from the upright, operating position to a non-upright position, the possibility of water flowing from the humidification chamber and out through the humidifier inlet is discouraged or prevented.*

*10. The humidifier according to claim 8, wherein the humidifier further includes a downwardly extending divider wall positioned adjacent an outlet of the gas introduction chamber.*

*11. The humidifier according to claim 8, wherein the gas introduction chamber is positioned above the water when the base retains a predetermined maximum volume of water and is in the upright, operating position.*

*12. The humidifier according to claim 8, wherein the humidifier includes a vertical passage of closed cross-sectional shape constructed to guide the flow of pressurized breathable gas from the gas introduction chamber to the humidification chamber.*

*13. The humidifier according to claim 12, wherein the gasket and at least a portion of the vertical passage is formed as an integrated unit.*

*14. The humidifier according to claim 8, wherein the gasket includes a closed vertical passage adapted to guide the flow of pressurized breathable gas from the gas introduction chamber to the humidification chamber.*

*15. The humidifier according to claim 8, wherein a volume of the gas introduction chamber is smaller than a volume of the humidification chamber.*

*16. The humidifier according to claim 15, wherein the volume of the humidification chamber is greater than a predetermined maximum volume of water contained in the base.*

*17. The humidifier according to claim 8, wherein:*

*the humidifier inlet and the humidifier outlet are configured to be positioned above the water when the base retains a predetermined maximum volume of water and the humidifier is in the upright, operating position,*

*the gas introduction chamber and the humidification chamber are configured so that when the base retains the predetermined maximum volume of water and the humidifier is rotated around a horizontal axis parallel to a bottom surface of the humidifier, from the upright, operating position to a non-upright position, the possibility of water flowing from the humidification chamber and out through the humidifier inlet is discouraged or prevented,*

*the humidifier further includes a downwardly extending divider wall positioned adjacent an outlet of the gas introduction chamber,*

*the gas introduction chamber is positioned above the water when the base retains the predetermined maximum volume of water and is in the upright, operating position,*

*the humidifier includes a vertical passage of closed cross-sectional shape constructed to guide the flow of pressurized breathable gas from the gas introduction chamber to the humidification chamber, the vertical passage being formed as part of the gasket,*

*a volume of the gas introduction chamber is smaller than a volume of the humidification chamber,*

*the volume of the humidification chamber is greater than the predetermined maximum volume of water.*

*18. The humidifier according to claim 8, wherein the heat conducting metallic material comprises a metallic plate having a horizontal portion and an upstanding wall along at least a portion of the metallic plate, the upstanding wall having a lip positioned at a distal end of the upstanding wall, the lip extending generally parallel to the horizontal portion of the plate.*

*19. The humidifier according to claim 18, further comprising a resilient seal member positioned at a junction where the metallic plate and aside wall portion of the base meet.*

*20. A CPAP system including a blower to generate the flow of pressurized breathable gas and the humidifier according to claim 8.*

*21. A CPAP system including:*

*a CPAP apparatus having a blower to generate the flow of pressurized breathable gas; and*

*a housing with a humidifier receptacle within which the humidifier of claim 8 is removably disposed.*

*22. The CPAP system according to claim 21, wherein the blower and the housing are rigidly connected together.*

*23. The CPAP system according to claim 21, wherein the housing has a base portion including the heating element and a retaining portion configured to secure the humidifier in position, the retaining portion extending substantially parallel to the base portion and being positioned above the top cover, the retaining portion having a downwardly facing surface that engages an exterior portion of the humidifier, wherein the humidifier inlet is positioned to receive the flow of pressurized breathable gas once the humidifier is loaded into the humidifier receptacle.*

*24. The CPAP system according to claim 23, further comprising a securing mechanism that releasably locks the humidifier in the humidifier receptacle.*

*25. The CPAP system according to claim 24, wherein the securing mechanism includes at least one movable locking lug that is movable between a locked position in engagement with the housing and an unlocked position, the securing mechanism further including a biased member that supports the at least one movable locking lug, the biased member being manually operable to move the lug from the locked position to the unlocked position, thereby allowing the humidifier to be withdrawn from the humidifier receptacle.*

*26. A humidifier assembly for a CPAP apparatus, comprising:*

*the humidifier according to claim 8;*

*a housing providing a receptacle within which the humidifier is at least partly disposed in a removable manner by horizontally inserting the humidifier within and pulling it out of the receptacle, the housing comprising a base portion forming a lower surface of the receptacle and configured to support the humidifier thereon, the base portion including the heating element adapted to be in thermal contact with the heat conducting metallic plate of the base when the humidifier is disposed in the receptacle,*

*a retaining portion configured to secure the humidifier in position relative to the housing, the retaining portion extending substantially parallel to the base portion and being spaced above the lower surface of the base portion, the retaining portion having a downwardly facing surface that engages an exterior portion of the humidifier as the humidifier is horizontally loaded into the receptacle, the retaining portion being positioned to constrain the humidifier such that, during assembly, the heat conducting metallic plate of the base of the humidifier slides against the heating element, wherein the humidifier inlet of the humidifier is provided at a rear wall of the humidifier and is positioned to receive the flow of pressurized breathable gas once the humidifier is loaded into the receptacle; and*

*a securing mechanism that releasably locks the humidifier at least partly in the receptacle.*

*27. The humidifier assembly according to claim 26, wherein the at least one securing mechanism includes a pair of locking lugs formed on the humidifier, each of the lugs being configured to be received in a respective recess of the housing once the humidifier is inserted to the housing.*

*28. The humidifier assembly according to claim 25, wherein the top cover includes an upper portion having an external recess.*

*29. The humidifier assembly according to claim 26, wherein at least a portion of the humidifier remains exposed when the humidifier is received within the receptacle.*

*30. The humidifier assembly according to claim 26, wherein the heating element is a flat plate-like resistance heater.*

*31. The humidifier assembly according to claim 26, wherein the securing mechanism includes a plurality of locking lugs formed on the humidifier and plurality of recesses provided in the housing, wherein the humidifier is structured for connecting to the housing by moving the humidifier in a generally horizontal direction relative to the housing until a fully inserted position is achieved, at which position the lugs are moveable in a generally vertical direction into the respective recesses, to therefore lock the humidifier against withdrawal from the housing.*

*32. The humidifier assembly according to claim 31, wherein each lug positively engages with a side wall surface of the respective recess when in the fully inserted position, each said side wall surface extending in the generally vertical direction.*

*33. The humidifier assembly according to claim 32, further comprising a biasing element to bias the locking lugs into the respective recesses.*

*34. The humidifier assembly according to claim 33, wherein, to allow removal of the humidifier from the housing, the biasing element is manually movable to allow the lugs to withdraw from engagement with the recesses, at which point the humidifier is pulled out from the housing in the generally horizontal direction.*

*35. The humidifier assembly according to claim 26, wherein a predetermined maximum volume of water is contained entirely in the humidification chamber when the humidifier within the housing is in the upright operating orientation.*

*36. The humidifier assembly according to claim 26, wherein the housing includes an upstanding wall portion extending in a substantially vertical orientation compared to the base portion of the housing, the rear wall being positioned proximate the upstanding wall portion when the humidifier is fully inserted relative to the housing, the upstanding wall portion including an opening in the wall that aligns with the humidifier inlet of the humidifier when the humidifier is fully inserted relative to the housing, the opening being configured to allow communication of the flow of pressurized breathable gas from an outlet of the CPAP apparatus to the humidifier inlet of the humidifier.*

*37. The humidifier assembly according to claim 36, wherein the humidifier inlet of the humidifier comprises a generally cylindrical tube.*

*38. A CPAP system including the CPAP apparatus and the humidifier assembly of claim 26.*

*39. The CPAP system according to claim 38, wherein the CPAP apparatus includes a controller to control the heating element.*

*40. A humidifier for humidifying a flow of pressurized breathable gas to be delivered to a patient, the humidifier comprising:*

*a humidifier body configured to retain a body of liquid having a predetermined maximum volume, the humidifier body comprising:*

*a humidifier body inlet configured to receive a flow of pressurized breathable gas;*

*a humidifier body outlet adapted to deliver the flow of pressurized breathable gas with added humidity;*

*a gas introduction chamber having a gas introduction chamber inlet, the gas introduction chamber inlet being adapted to receive the flow of pressurized breathable gas from the humidifier body inlet;*

*a humidification chamber in communication with the gas introduction chamber and the humidifier body outlet, the humidification chamber having a bottom surface comprising heat conductive metallic material,*

*a vertical passage of closed cross sectional shape connecting the gas introduction chamber to the humidification chamber, the vertical passage being configured to direct the flow of pressurized breathable gas in a downwards direction towards an approximate center of the humidification chamber, and*

*a cover that defines an upper boundary of both the gas introduction chamber and at least a portion of the humidification chamber, the cover including the humidifier body outlet, wherein:*

*the gas introduction chamber inlet faces a horizontal direction when the humidifier is in an upright, operating position,*

*the humidification chamber comprises a bottom portion below the gas introduction chamber when the humidifier is in the upright, operating position, and comprises a side portion beside the gas introduction chamber when the humidifier is in the upright, operating position,*

*the entire gas introduction chamber is positioned above the body of liquid when the humidifier body*

*retains the predetermined maximum volume of liquid and is in the upright, operating position, and*

*the gas introduction chamber and the humidification chamber are configured so that the possibility of liquid flowing from the humidification chamber and out through the humidifier body inlet is discouraged or prevented when the humidifier body retains the maximum volume of liquid and is rotated from the upright, operating position to a non-upright position that would otherwise tend to direct liquid back towards the humidifier body inlet.*

*41. The humidifier according to claim 40, wherein:*

*a volume of the gas introduction chamber is smaller than a volume of the humidification chamber,*

*the humidifier body inlet and the humidifier body outlet are positioned on opposite sides of the humidifier body,*

*the volume of the humidification chamber is greater than the predetermined maximum volume of liquid,*

*a maximum level of liquid in the humidifier body remains below both the gas introduction chamber inlet and an outlet of the gas introduction chamber in the upright, operating position, and*

*the humidifier body inlet being positioned on a rear side wall of the humidifier body.*

*42. The humidifier according to claim 40, wherein the gas introduction chamber is positioned to receive the flow of pressurized breathable gas from the humidifier body inlet of the humidifier, the gas introduction chamber being oriented to direct the pressurized breathable gas in a substantially horizontal direction when the humidifier is in the upright working orientation, the humidifier further including a substantially vertically extending passage oriented to direct the pressurized breathable gas from the gas introduction chamber in a downward direction towards liquid contained in the humidification chamber.*

*43. The humidifier according to claim 42, wherein the non-upright position includes an up-ended position in which a rear side wall of the humidifier is vertically below a front side wall of the humidifier, whereby even if a liquid level within the humidifier is higher than the inlet of the humidifier, liquid is discouraged or prevented from exiting through the humidifier body inlet.*

*44. The humidifier according to claim 40, wherein the humidifier body includes a base to contain the predetermined maximum volume of liquid, the base being movably connected to the cover via a snap fit connection.*

*45. The humidifier according to claim 40, wherein at least a portion of the humidifier remains exposed when the humidifier is received within a humidifier receptacle.*

*46. The humidifier according to claim 40, wherein the humidifier body includes a rear side wall including the humidifier body inlet, the rear wall extending in a substantially vertical direction when the humidifier is in the upright working orientation.*

*47. The humidifier according to claim 40, wherein the gas introduction chamber is positioned to receive the flow of pressurized breathable gas from the humidifier body inlet of the humidifier body, the gas introduction chamber is oriented to direct the flow of pressurized breathable gas in a substantially horizontal direction when the humidifier is in the upright working orientation, and the humidifier further includes a vertical passage communicating the gas introduction chamber with the humidification chamber, and*

*wherein the non-upright position includes a position in which the humidifier body inlet faces downward and the vertical passage is positioned at a level higher than the humidifier body inlet, whereby liquid is discouraged or prevented from moving from the humidification chamber and exiting through the humidifier body inlet.*

*48. The humidifier according to claim 40, wherein:*

*a volume of the gas introduction chamber is smaller than a volume of the humidification chamber,*

*the humidifier body inlet and the humidifier body outlet are positioned on opposite sides of the humidifier body,*

*the volume of the humidification chamber is greater than the predetermined maximum volume of liquid,*

*a maximum level of liquid in the humidifier body remains below both the gas introduction chamber inlet, an outlet of the gas introduction chamber and the vertical passage in the upright, operating position,*

*the humidifier body inlet is positioned on a rear side wall of the humidifier body,*

*the gas introduction chamber is positioned to receive the flow of pressurized breathable gas from the humidifier inlet, the gas introduction chamber being oriented to direct the pressurized breathable gas in a substantially horizontal direction when the humidifier body is in the upright working orientation, the humidifier body further including a guide oriented to direct the flow of pressurized breathable gas from the gas introduction chamber in a downward direction towards liquid contained in the humidification chamber,*

*the humidifier body further comprises a base and a snap fit clip to detachably connect the base and the cover,*

*the rear sidewall extends in a substantially vertical direction when the humidifier is in the upright working orientation, and*

*the non-upright position includes a position in which the humidifier body inlet faces downward, whereby liquid is discouraged or prevented from moving from the humidification chamber and exiting through the humidifier body inlet.*

*49. The humidifier according to claim 40, wherein:*

*a volume of the gas introduction chamber is smaller than a volume of the humidification chamber,*

*the volume of the humidification chamber is greater than the predetermined maximum volume of liquid,*

*a maximum level of liquid in the humidifier body remains below both the gas introduction chamber inlet and the gas introduction chamber outlet in the upright, operating position,*

*the humidifier body inlet being positioned on a side wall of the humidifier body,*

*the gas introduction chamber is positioned to receive the flow of pressurized breathable gas from the humidifier body inlet, the gas introduction chamber being oriented to direct the flow of pressurized breathable gas in a substantially horizontal direction when the humidifier is in the upright working orientation, the humidifier further including a substantially vertically extending passage oriented to direct the pressurized breathable gas from the gas introduction chamber in a downward direction towards liquid contained in the humidification chamber,*

*wherein the humidifier further comprises base to contain the liquid and a snap fit clip to detachably connect the base and the cover,*

*the side wall extends in a substantially vertical direction when the humidifier is in the upright working orientation, and*

*the non-upright position includes a position in which the inlet faces downward and the passage is positioned at*

*a level higher than the humidifier body inlet, whereby liquid is discouraged or prevented from moving from the humidification chamber and exiting through the humidifier body inlet.*

*50. A CPAP system including a blower to generate a flow of pressurized breathable gas and the humidifier according to claim 40.*

* * * * *